(12) United States Patent  
Feld

(10) Patent No.: US 11,903,832 B2  
(45) Date of Patent: Feb. 20, 2024

(54) TRANSCATHETER ARTIFICIAL CUSP FOR VALVE INSUFFICIENCY

(71) Applicant: Cuspa Ltd., Nazareth (IL)

(72) Inventor: Yair Feld, Haifa (IL)

(73) Assignee: Cuspa Ltd., Nazareth (IL)

( * ) Notice: Subject to any disclaimer, the term of this patent is extended or adjusted under 35 U.S.C. 154(b) by 0 days.

(21) Appl. No.: 17/259,704

(22) PCT Filed: Jul. 28, 2019

(86) PCT No.: PCT/IL2019/050853  
§ 371 (c)(1),  
(2) Date: Jan. 12, 2021

(87) PCT Pub. No.: WO2020/026234  
PCT Pub. Date: Feb. 6, 2020

(65) Prior Publication Data  
US 2021/0338418 A1    Nov. 4, 2021

Related U.S. Application Data

(60) Provisional application No. 62/711,532, filed on Jul. 29, 2018.

(51) Int. Cl.  
*A61F 2/24* (2006.01)

(52) U.S. Cl.  
CPC ............ *A61F 2/246* (2013.01); *A61F 2/2463* (2013.01); *A61F 2/2466* (2013.01); *A61F 2220/0025* (2013.01); *A61F 2220/0075* (2013.01)

(58) Field of Classification Search  
CPC ....... A61F 2/246; A61F 2/2463; A61F 2/2466  
See application file for complete search history.

(56) References Cited

U.S. PATENT DOCUMENTS

| | | | |
|---|---|---|---|
| 6,797,002 B2 * | 9/2004 | Spence | A61F 2/2457 623/2.38 |
| 9,414,918 B2 * | 8/2016 | Chau | A61F 2/243 |
| 2013/0310928 A1 * | 11/2013 | Morriss | A61F 2/2457 623/2.18 |
| 2013/0338764 A1 | 12/2013 | Thornton et al. | |
| 2014/0067048 A1 | 3/2014 | Chau et al. | |
| 2014/0067052 A1 | 3/2014 | Chau et al. | |

(Continued)

FOREIGN PATENT DOCUMENTS

| | | |
|---|---|---|
| CN | 104768500 | 7/2015 |
| WO | 2017/217932 | 12/2017 |

OTHER PUBLICATIONS

International Search Report for PCT/IL2019/050853 dated Dec. 3, 2019, 3 pages.

(Continued)

*Primary Examiner* — William H Matthews

(57) ABSTRACT

The present invention relates to an obstructing device comprising a hollow tubular member comprising a. a proximal opening at its proximal end; b. a substantially tubular surface extending distally from said proximal opening; c. a distal end. The obstructing device further comprises a grasping arm extending distally from said opening at the proximal end; wherein the distal end is either closed or comprises a small orifice. The present invention relates to a method of delivery of said device.

31 Claims, 25 Drawing Sheets

(56) References Cited

U.S. PATENT DOCUMENTS

| | | | |
|---|---|---|---|
| 2014/0179993 A1 | 6/2014 | Alexander et al. | |
| 2015/0230919 A1 | 8/2015 | Chau et al. | |
| 2016/0310268 A1 | 10/2016 | Oba | |
| 2017/0143481 A1 | 5/2017 | Morriss et al. | |
| 2017/0172741 A1 | 6/2017 | Subramanian et al. | |
| 2017/0189174 A1 | 7/2017 | Braido et al. | |
| 2017/0360559 A1* | 12/2017 | Mayer | A61F 2/2421 |
| 2018/0185154 A1* | 7/2018 | Cao | A61B 17/1227 |

OTHER PUBLICATIONS

Written Opinion of the ISA for PCT/IL2019/050853 dated Dec. 3, 2019, 6 pages.
Extended European Search Report dated Mar. 23, 2022 in corresponding European Application No. 19844580.1, 8 pages.
Notification of Office Action and Search Report dated Jul. 28, 2023 From the National Intellectual Property Administration of the People's Republic of China Re. Application No. 201980051100.8 and Its English Summary and Machine Translation. (32 Pages).
Notice of Reason(s) for Rejection dated May 24, 2023 From the Japan Patent Office Re. Application No. 2021-502591. (3 pages).
Translation Dated Jun. 22, 2023 of Notice of Reason(s) for Rejection dated May 24, 2023 From the Japan Patent Office Re. Application No. 2021-502591. (4 pages).

* cited by examiner

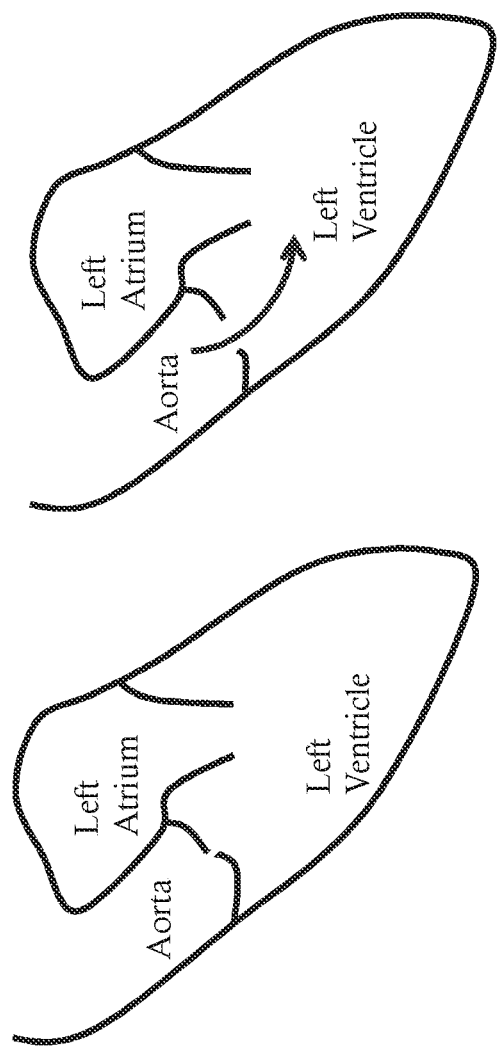

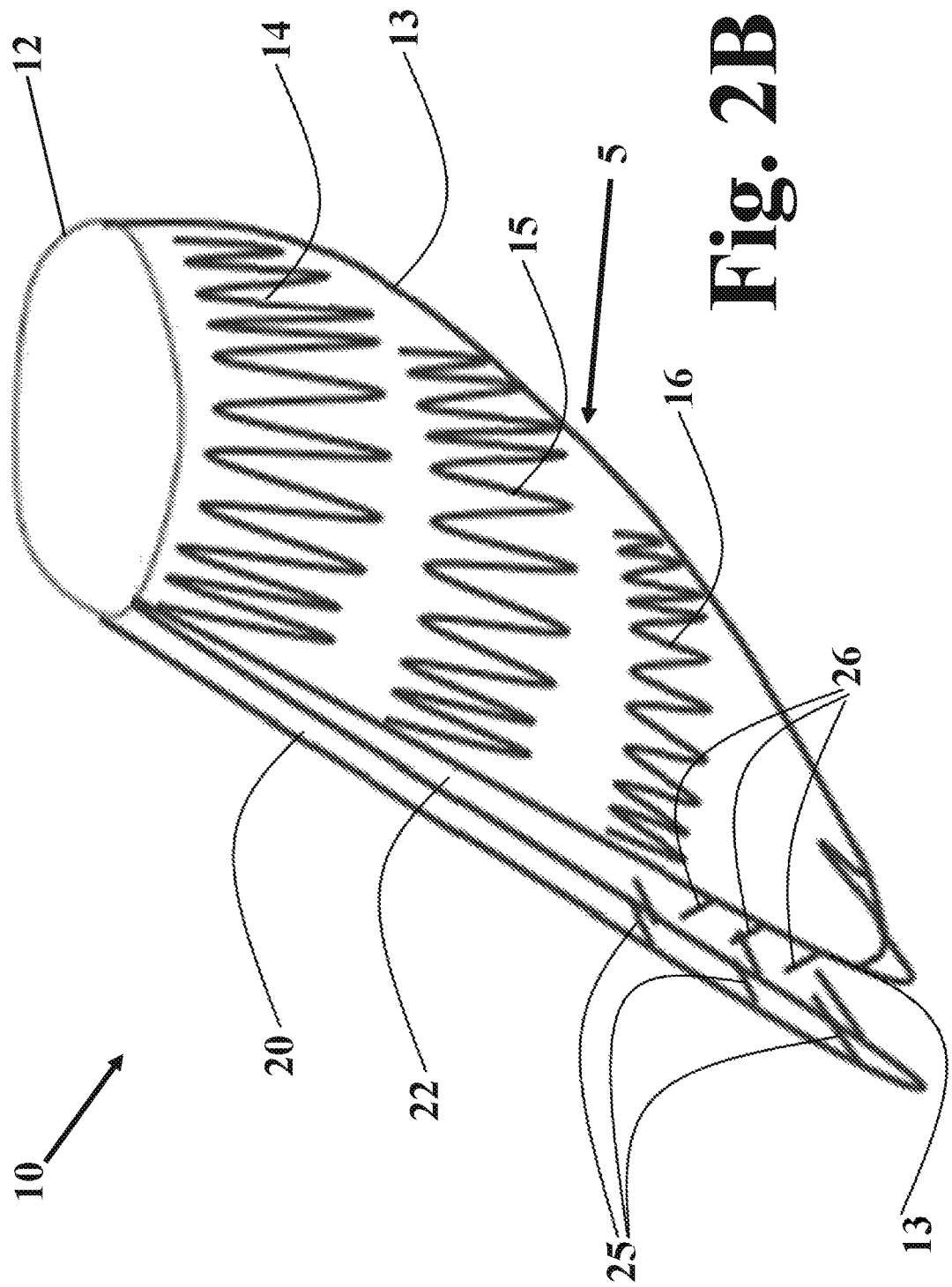

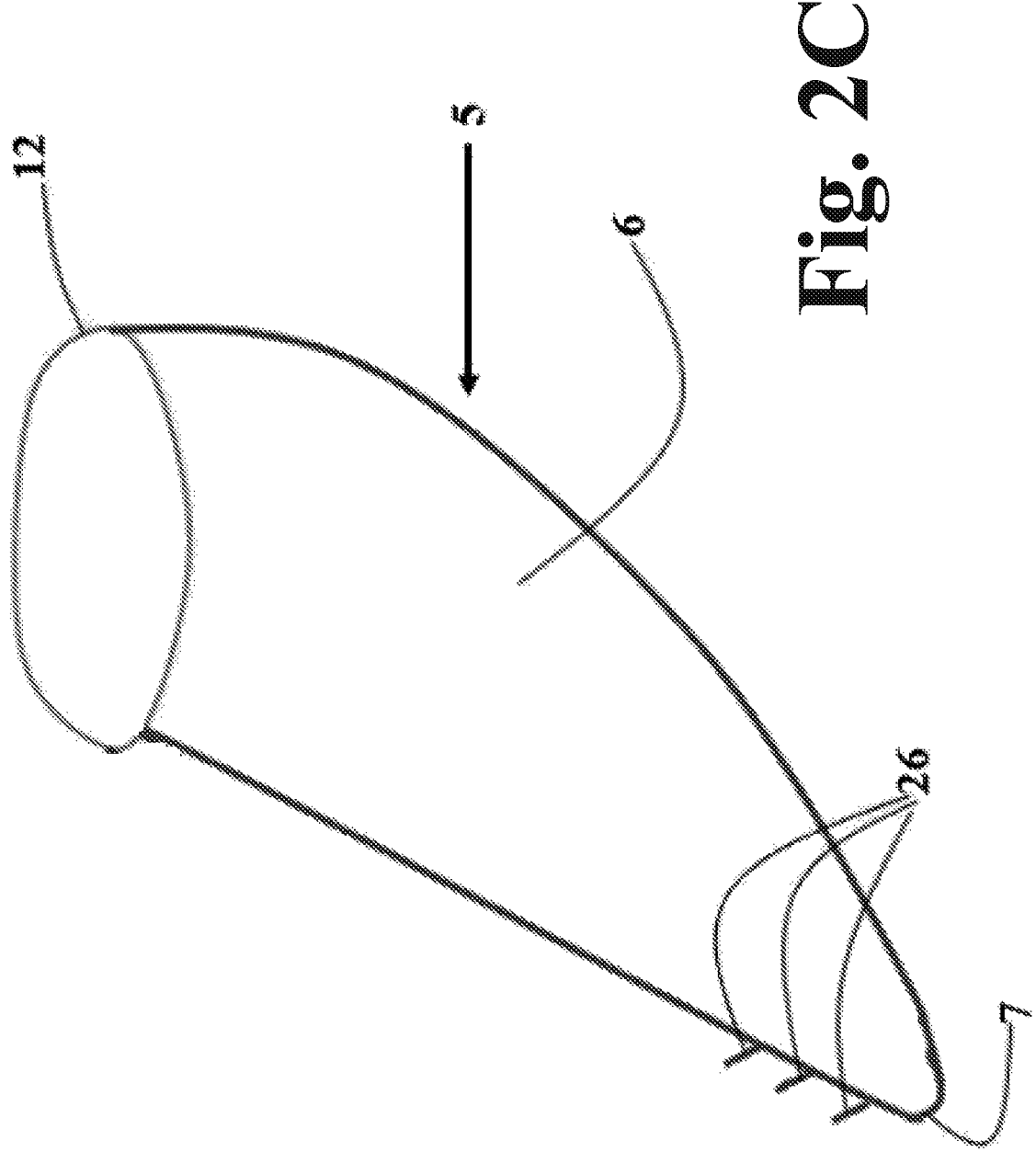

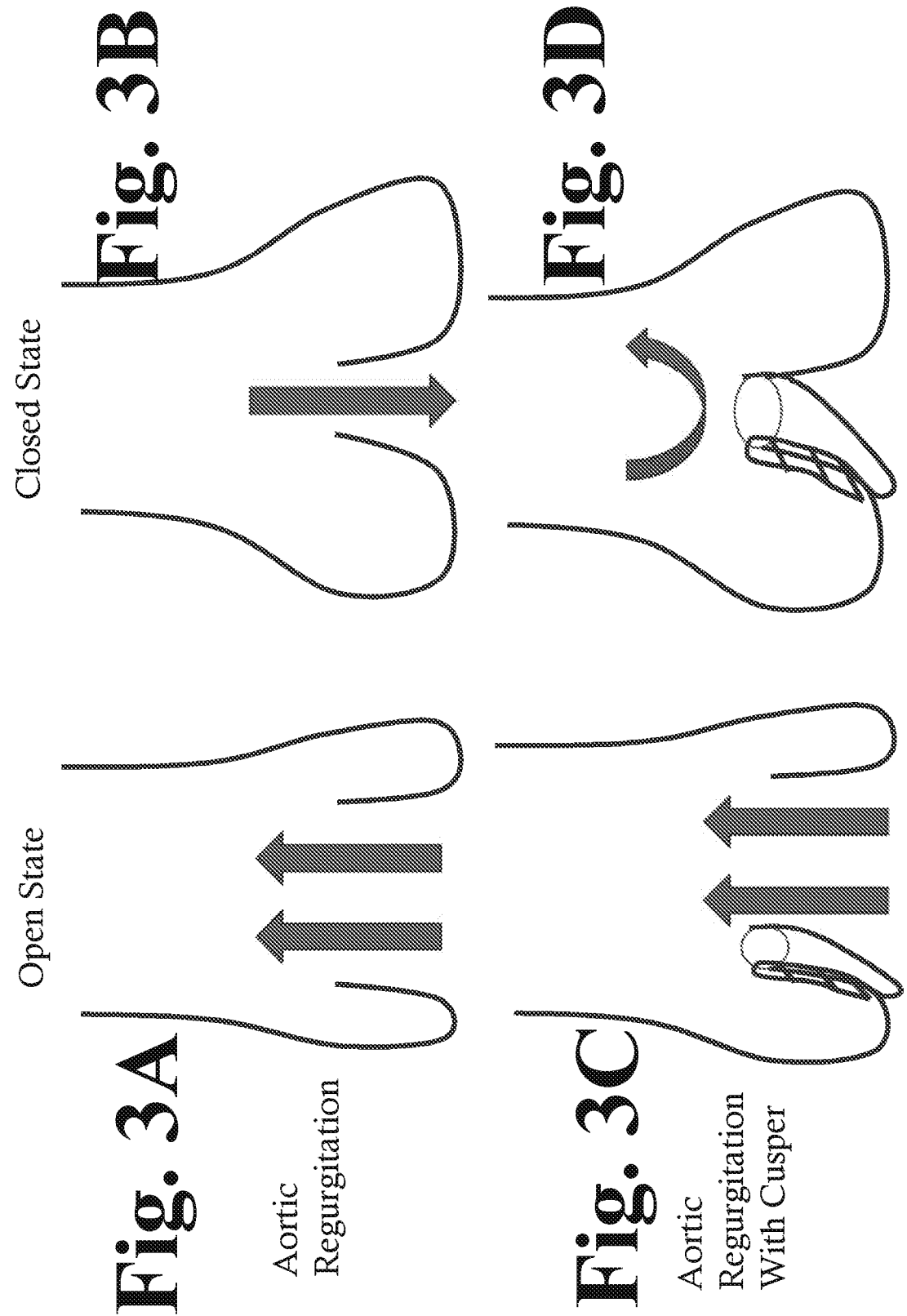

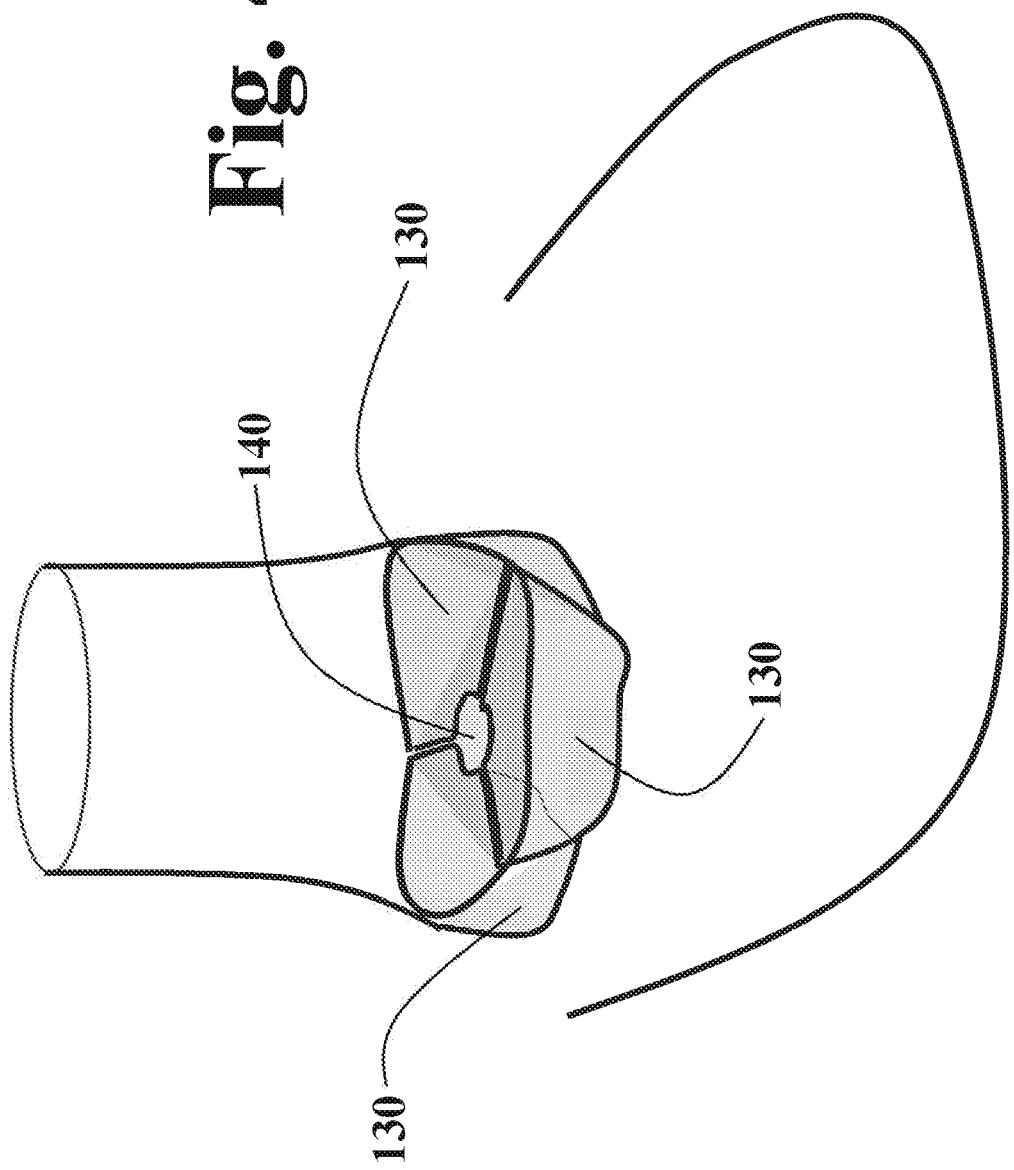

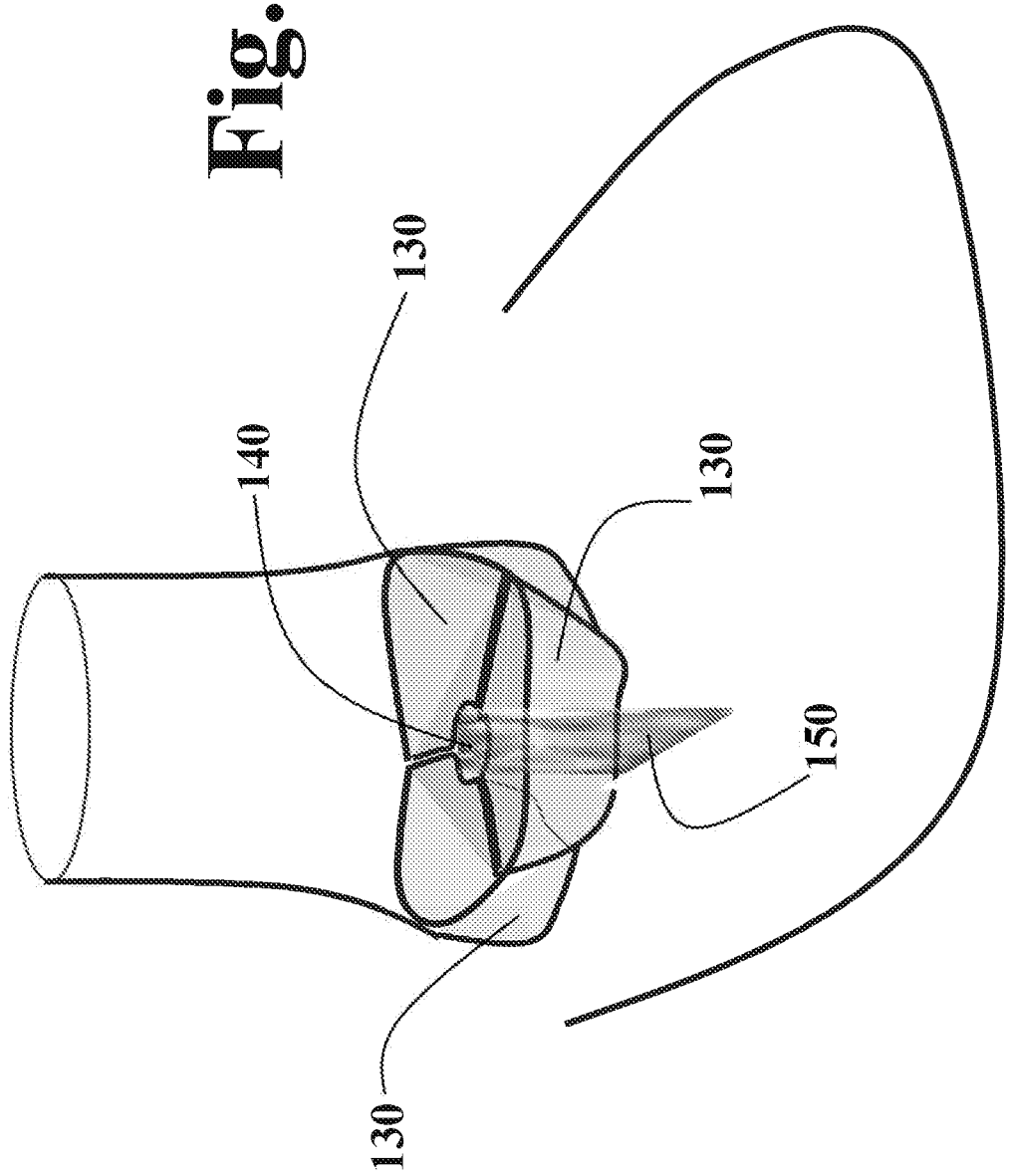

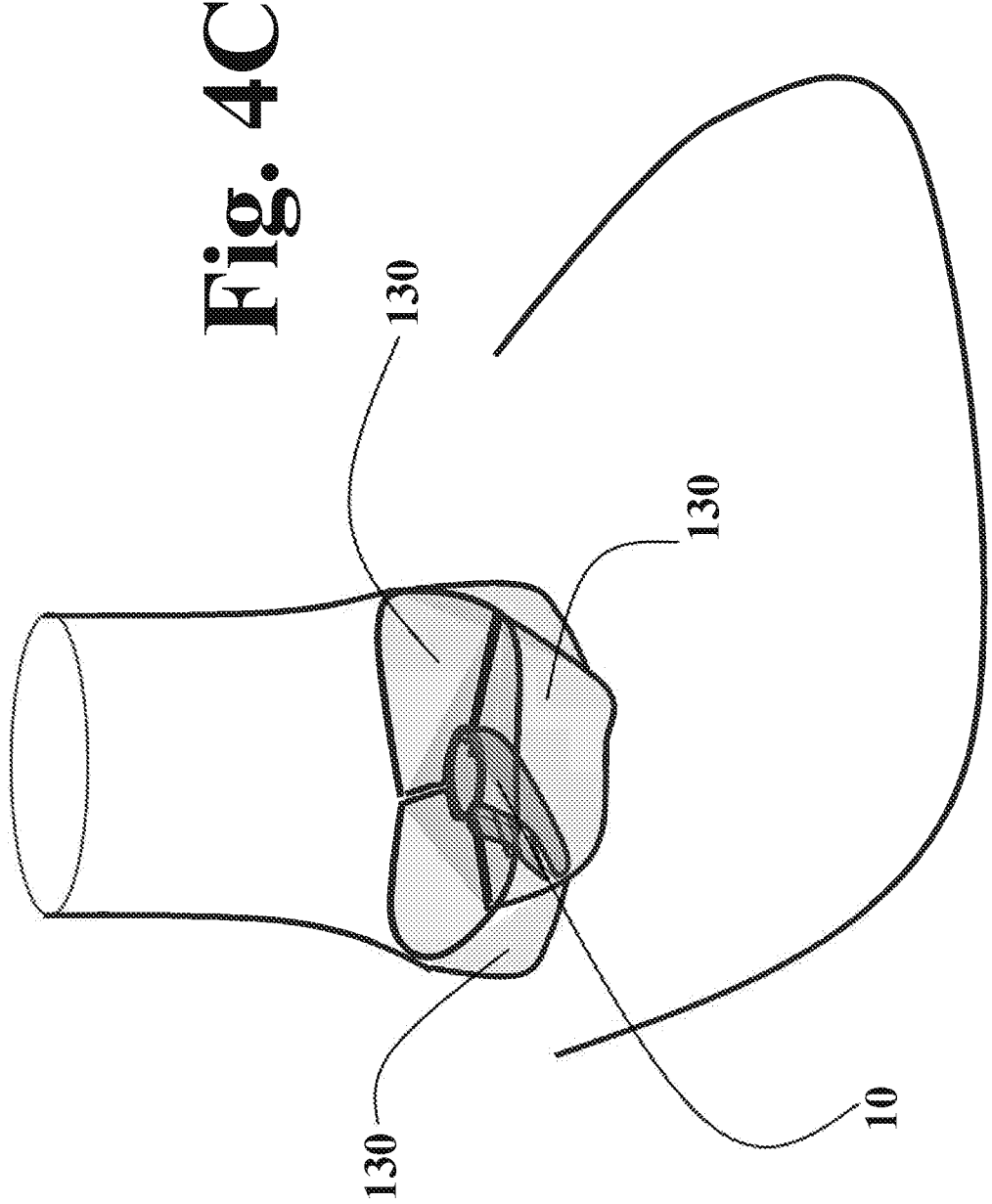

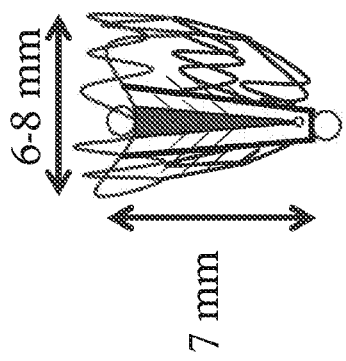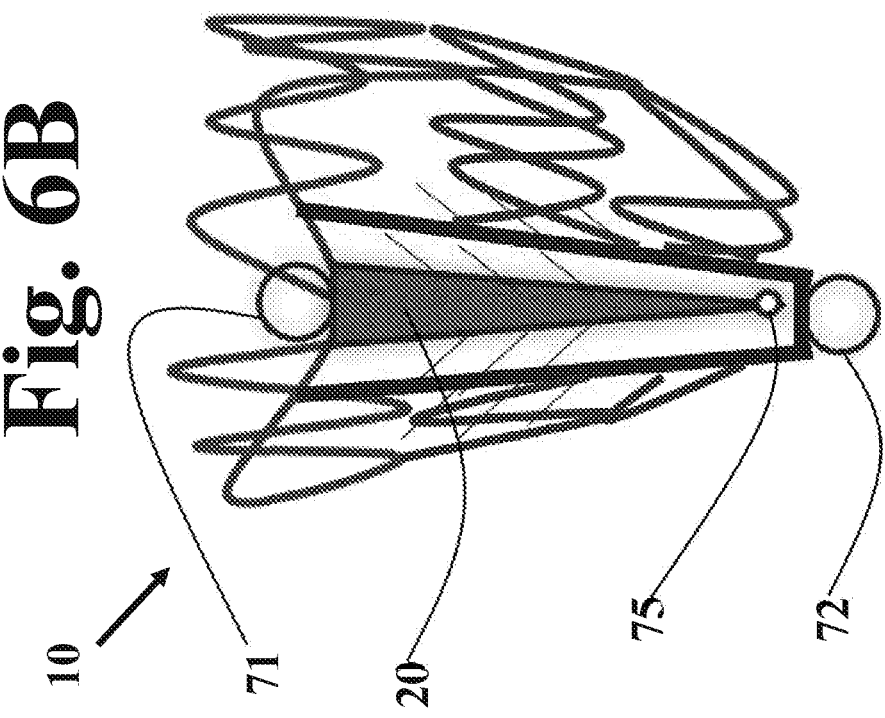

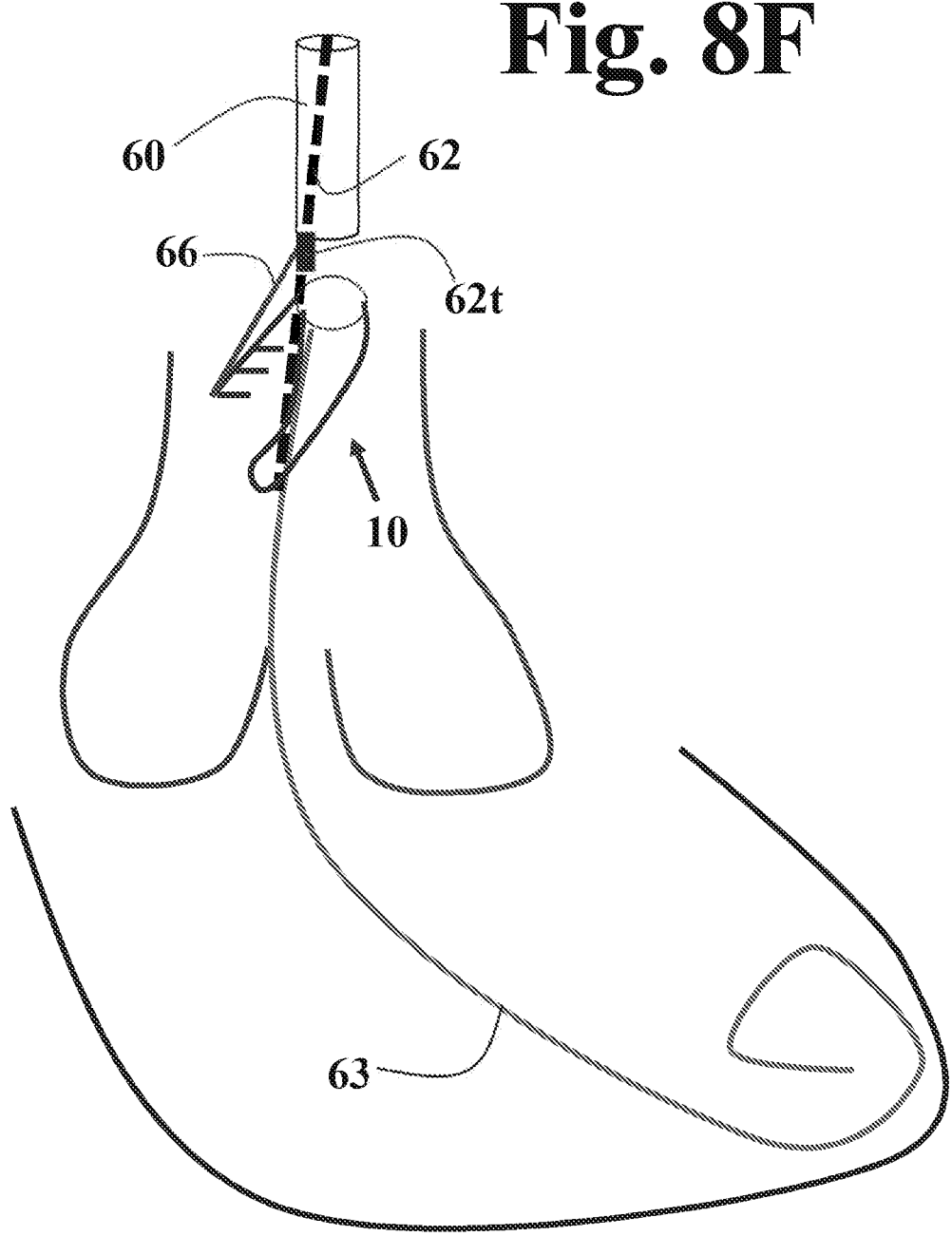

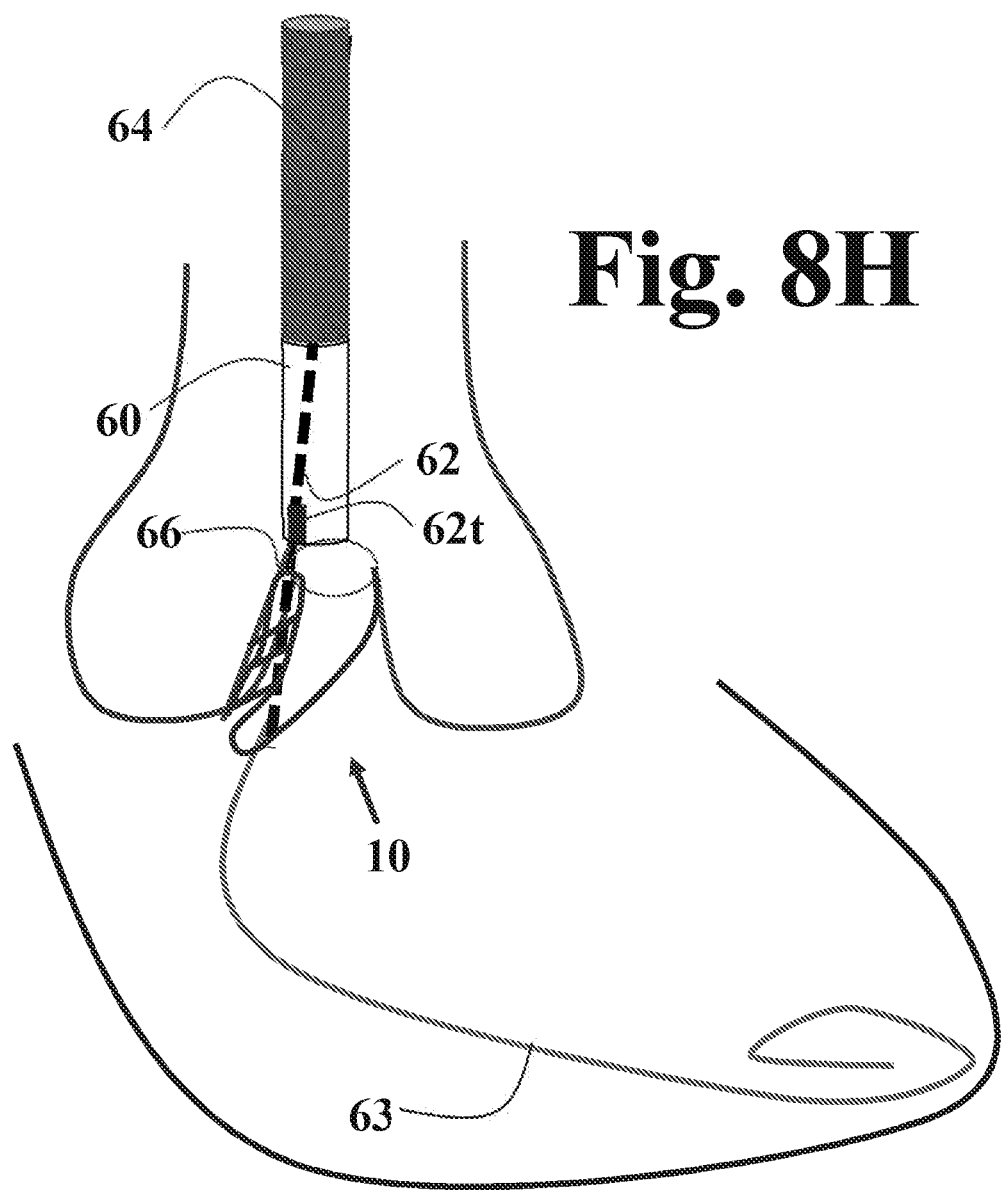

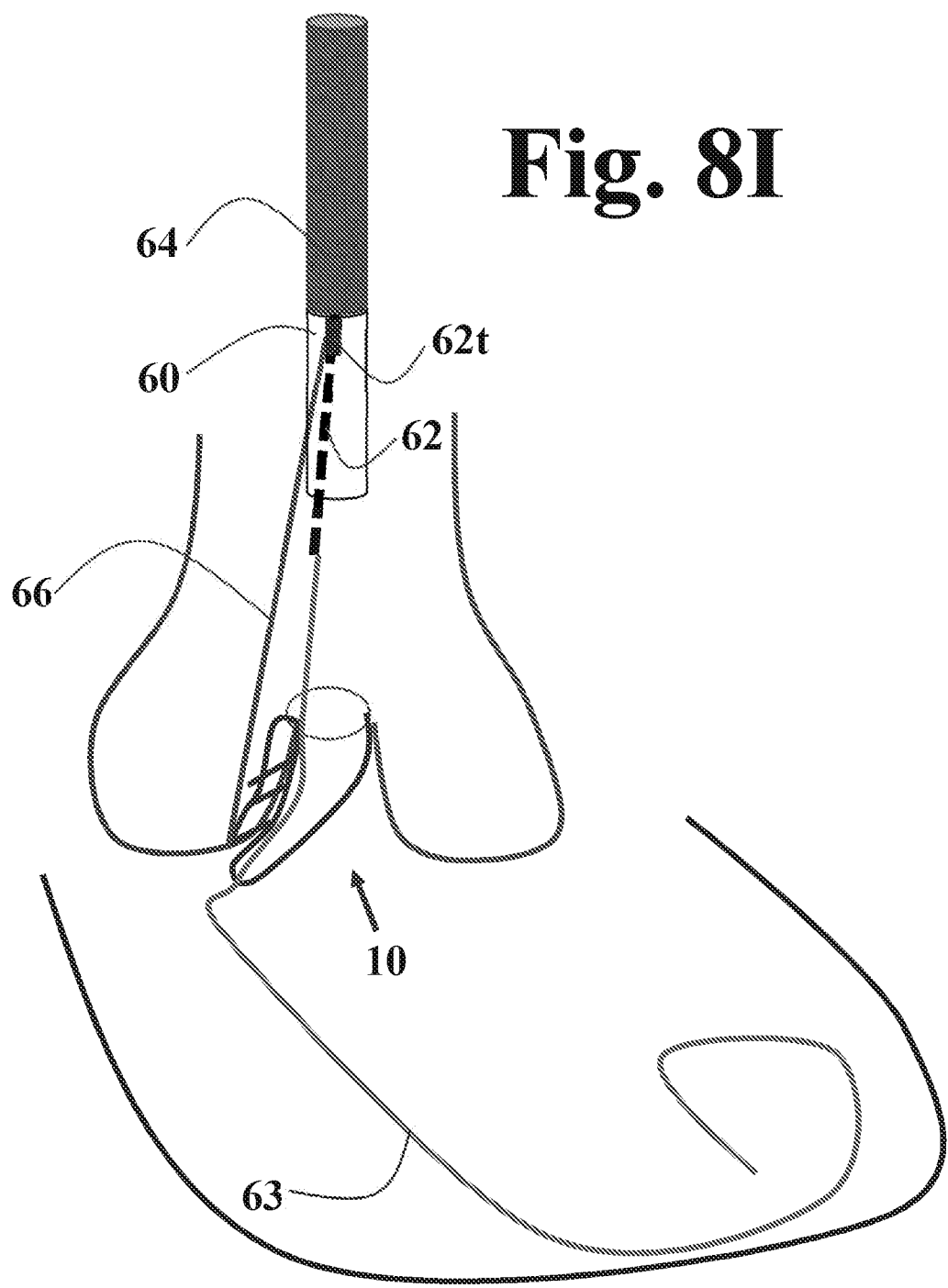

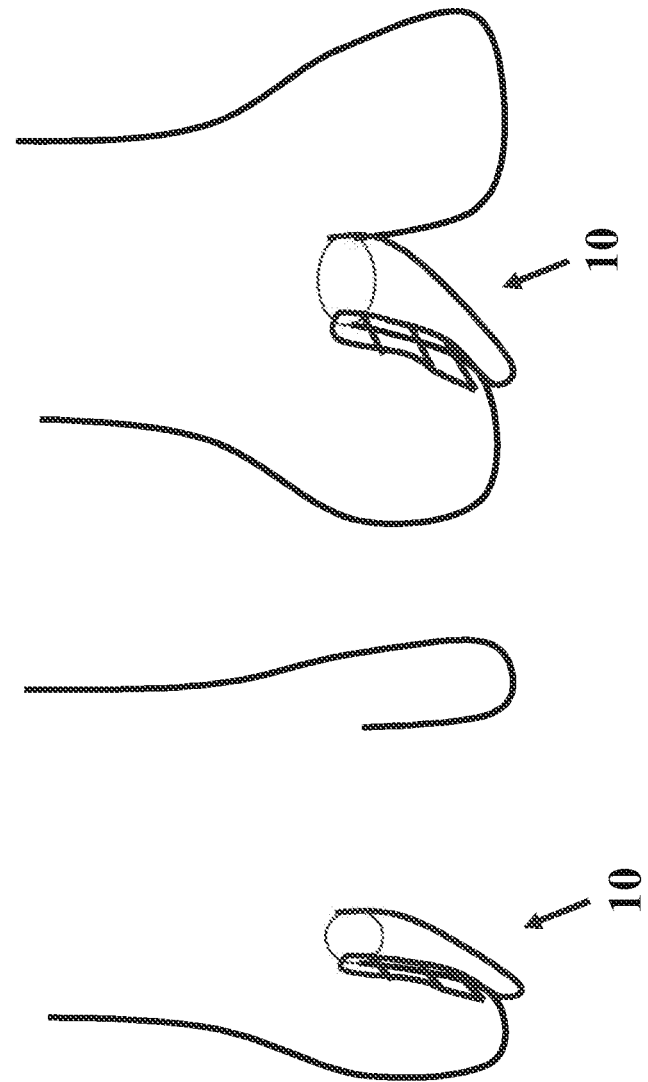

TRANSCATHETER ARTIFICIAL CUSP FOR VALVE INSUFFICIENCY

This application is the U.S. national phase of International Application No. PCT/IL2019/050853 filed Jul. 28, 2019 which designated the U.S. and claims priority to U.S. Provisional Application No. 62/711,532 filed Jul. 29, 2018, the entire contents of each of which are hereby incorporated by reference.

FIELD OF THE INVENTION

The present invention relates to the field of medical devices. More particularly, the present invention relates to an artificial cusp for trans-catheter treatment of valve insufficiency.

BACKGROUND OF THE INVENTION

Valvular insufficiency is the results of valve leakage when the valve is in a closed state. The 4 valvular insufficiencies are Aortic regurgitation (AR), mitral regurgitation (MR), tricuspid regurgitation (TR), and pulmonary regurgitation (PR). The main treatment for these pathologies, when they are in a state causing symptoms or significant cardiac remodeling, is valve replacement through open heart surgery, or in some cases catheter-based therapy. However, these treatments are limited to MR only, and TR, under specific conditions.

For example, the aortic valve lies between the left ventricle and the aorta. When the left ventricle contracts during each heartbeat (systole), pressure rises in the left ventricle. When the pressure in the left ventricle rises above the pressure in the aorta, the aortic valve opens, allowing blood to exit the left ventricle into the aorta. The left ventricle actually pushes blood through three flexible cuplike leaflets which make up the aortic valve. When the left ventricle relaxes (when ventricular systole ends) pressure in the left ventricle rapidly drops and the aortic pressure forces the aortic valve to close. The aortic valve closes and prevents blood from flowing back to the left ventricle.

However, in the case of AR, valve leakage occurs when the aortic valve is in a closed state. The leaflets partially close in the aortic valve in the close state, leaving a portion of the aortic valve opened (regurgitant orifice), what causes a portion of the blood to flow back into the left ventricle. This necessitates the heart to work harder, causing a deterioration to the health of a patient. FIG. 1A shows an example of a healthy normal heart where the aortic valve is fully closed. FIG. 1B shows an example of AR with an abnormal aortic valve which fails to fully close allowing the blood to leak backwards into the left ventricle.

Similar leakages occur to the mitral (bicuspid) valve, the tricuspid valve and the pulmonary valve in cases of MR, TR and PR, respectively, mutatis mutandis.

US 2015/0230919 A1 Describes a method for leaflet prolongation of the mitral or tricuspid valve. The device is implanted around the leaflet therefore extending it and potentially closing the malcoaptation gap.

However, the prior art approaches may be highly invasive and risky procedures. The heart in prior art approaches based on implantations may be non-tolerant to the implantation positions. Also, there is still a need for an improved efficient closure of the gap.

It is therefore an object of the present invention to provide a method and means for preventing blood leakages in cases of AR, MR, TR and PR.

It is further an object of the present invention to provide a device that prevents the aforementioned blood leakages.

It is yet a further object of the present invention to provide a method of delivery thereof.

Other objects and advantages of the present invention will become apparent as the description proceeds.

SUMMARY OF THE INVENTION

The present invention relates to a device for alleviating valvular insufficiency. The present invention relates to the treatment of valvular insufficiency by attaching an artificial valve cusp to a native or artificial cusp or leaflet. By doing this it improves heart function by preventing or reducing valve leakage. The artificial cusp is collapsible to prevent valve stenosis when the valve is in an open state.

The present invention relates to an obstructing device comprising a hollow tubular member having an opening and a grasping elongated arm extending from the opening such that a small gap is formed between the grasping arm and the hollow tubular member. The obstructing device is mounted on a heart valve suffering from valvular insufficiencies (having a regurgitant orifice) on the heart valve cusp/leaflet. The obstructing device is mounted in a manner such that a side/wall of the cusp/leaflet is positioned within the small gap. This is carried out by angularly moving the grasping arm such that the gap substantially increases, placing the gap over a respective cusp/leaflet side/wall and angularly returning the grasping arm such that the gap decreases again, effectively mounting the device on the cusp/leaflet side/wall. The relatively wide opening of the obstructing device substantially closes the regurgitant orifice when the heart valve is in a closed state thus preventing blood leakage then.

The present invention relates to an obstructing device comprising:
  a hollow tubular member comprising:
    a. a proximal opening at its proximal end;
    b. a substantially tubular surface extending distally from said proximal opening;
    c. a distal end;
  a grasping arm extending distally from said opening at the proximal end;
  wherein the distal end is either closed or comprises a small orifice.

Preferably, the hollow tubular member comprises a membrane.

Preferably, the membrane is self-expandable.

Preferably, the obstructing device further comprises a frame comprising one or more wires;
  wherein the membrane is mounted on said frame.

Preferably, the hollow tubular member tappers distally.

Preferably, a thin gap is formed between the grasping arm and the substantially tubular surface.

Preferably, the grasping arm comprises a first group of connecting elements.

Preferably, the first group of connecting elements are selected from the group consisting of biocompatible needles, biocompatible pins and biocompatible spikes.

Preferably, the first group of connecting elements are biocompatible needles that extend proximally and slant from the grasping arm.

Preferably, the substantially tubular surface comprises a second group of connecting elements.

Preferably, the second group of connecting elements are selected from the group consisting of biocompatible needles, biocompatible pins and biocompatible spikes.

Preferably, the second group of connecting elements are biocompatible needles that extend proximally and slant from the substantially tubular surface.

Preferably, the obstructing device further comprises a proximal loop attached to the proximal opening.

Preferably, the obstructing device further comprises a distal loop attached to a distal portion of the hollow tubular member.

Preferably, the proximal loop and distal loop face each other and are aligned.

Preferably, the grasping arm comprises a loop at its distal end.

The present invention relates to a method for implanting an obstructing device as explained herein on a heart valve cusp or leaflet, wherein said obstructing device comprises a proximal loop attached to the proximal opening;
wherein said method comprises:
creating an opening in a blood vessel;
inserting an introducer sheath;
inserting a guide wire through the introducer sheath and passing it through the blood vessel all the way to the heart valve and therethrough to the respective heart chamber;
providing an inner sheath passing through the obstructing device proximal loop, and
providing that said inner sheath comprises a thickened portion placed proximal to said proximal loop,
passing the inner sheath over said guide wire until said device is placed prior to the respective heart valve;
providing a string inserted through the introducer sheath and passing via an opening in the inner sheath, and passing through the grasping arm loop and back via said opening in the inner sheath to the introducer sheath, such that both ends of said string extend from the introducer sheath,
pulling the two ends of said string proximally thereby opening the grasping arm;
positioning the obstructing device to the correct intended position;
pushing the obstructing device distally;
releasing said two ends of said string distally thereby causing the grasping arm to close;
proximally retrieving the inner sheath;
proximally retrieving one end of said string until said string exits the grasping arm loop and continuing to proximally retrieve said string until said string is fully retrieved;
proximally retrieving said guide wire;
removing said introducer sheath.

The present invention also relates to an obstructing device wherein said obstructing device comprises a hollow tubular member comprising:
a. a distal opening at its distal end;
b. a substantially tubular surface extending proximally from said distal opening;
c. a proximal end;
wherein said obstructing device further comprises a grasping arm extending proximally from said opening at the distal end;
wherein the proximal end is either closed or includes a small orifice.

Preferably, the grasping arm comprises a loop at its proximal end.

Preferably, the obstructing device comprises a proximal loop attached to a proximal portion of the hollow tubular member.

The present invention relates to a method for implanting an obstructing device on a heart valve cusp or leaflet,
wherein said obstructing device comprises a hollow tubular member comprising:
a. a distal opening at its distal end;
b. a substantially tubular surface extending proximally from said distal opening;
c. a proximal end;
wherein said obstructing device further comprises a grasping arm extending proximally from said opening at the distal end;
wherein the proximal end is either closed or includes a small orifice;
wherein the grasping arm comprises a loop at its proximal end; and
wherein said obstructing device comprises a proximal loop attached to a proximal portion of the hollow tubular member;
wherein said method comprises:
creating an opening in a blood vessel;
inserting an introducer sheath;
inserting a guide wire through the introducer sheath and passing it through the blood vessel all the way to the heart valve and therethrough to the respective heart chamber;
providing an inner sheath passing through the obstructing device proximal loop, and
providing that said inner sheath comprises a thickened portion placed proximal to said proximal loop,
passing the inner sheath over said guide wire until said device is placed in said respective heart chamber;
providing a string inserted through the introducer sheath and passing via an opening in the inner sheath distal to said distal loop, and passing through the grasping arm loop and back via said opening in the inner sheath to the introducer sheath, such that both ends of said string extend from the introducer sheath,
pulling the two ends of said string proximally thereby opening the grasping arm;
positioning the obstructing device to the correct intended position;
pulling the obstructing device proximally;
releasing said two ends of said string distally thereby causing the grasping arm to close;
proximally retrieving one end of said string until said string exits the grasping arm loop and continuing to proximally retrieve said string until said string is fully retrieved;
proximally retrieving the inner sheath;
proximally retrieving said guide wire;
removing said introducer sheath.

BRIEF DESCRIPTION OF THE DRAWINGS

The present invention is illustrated by way of example in the accompanying drawings, in which similar references consistently indicate similar elements and in which:

FIGS. 1A and 1B illustrate a normal functioning heart aortic valve and an Aortic Regurgitation functioning heart aortic valve respectively.

FIGS. 2A and 2B illustrate embodiments of the present invention.

FIG. 2C illustrates the hollow tubular member according to an embodiment of the present invention.

FIGS. 3A-3B illustrate the opening and closing of an aortic valve with Aortic Regurgitation in an open state and closed state respectively.

FIGS. 3C-3D illustrate the opening and closing of an aortic valve with the Aortic Regurgitation in an open state and closed state respectively as in FIGS. 3A-3B but functioning with the device according to an embodiment of the present invention.

FIGS. 4A-4C show a drawing of an Aortic Valve with Regurgitation alone, with blood leakage, and with the present invention, respectively

FIGS. 6A and 6B illustrate embodiments of the present invention.

DETAILED DESCRIPTION OF THE INVENTION

Figure 2A:
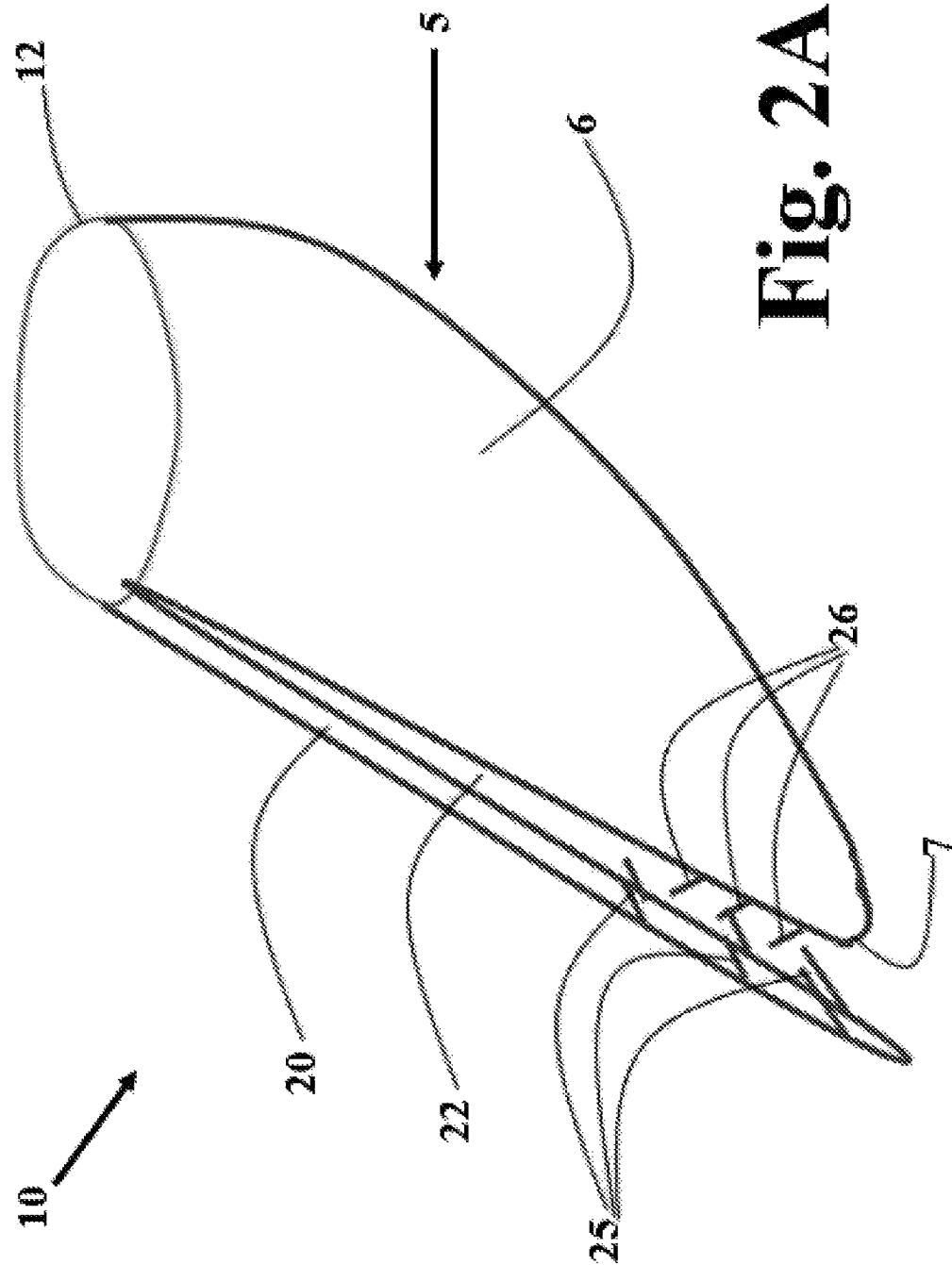

The present invention relates to an artificial cusp. More particularly, the present invention relates to a blood leakage obstructing device comprising a hollow tubular member, attachable to one of the heart native valves' (aortic valve, mitral valve, pulmonary valve, tricuspid valve) cusps/leaflets. The obstructing device effectively causes the heart native valve to be fully closed when in its closed state. The hollow tubular member can be seen as a scaffold to the cusps/leaflets, an add-on portion that moves with the cusp/leaflet as it opens and closes the valve. The device of the present invention is also referred to herein as "cusper device".

The device of the present invention will be explained in relation to the aortic valve, but may similarly be attached to the other heart native or artificial valves' cusps or leaflets, mutatis mutandis.

In the present specification the "proximal end" refers to the end closest to the medical personnel delivering the device. The "distal end" refers to the end furthest from the medical personnel and closest to the target location in the patient's body during delivery of the device. In relation to the embodiment which inserts the device of the present invention via the aorta (towards the left ventricle), the "distal direction" refers to the direction towards the left ventricle and the "proximal direction" refers to the opposite direction, i.e. the direction towards the aorta away from the left ventricle. Thus, the blood through the aortic valve flows from the distal to the proximal direction.

In cases with hearts having aortic valvular insufficiency, valve leakage occurs when the aortic valve is in a closed state. The leaflets/cusps partially close in the aortic valve in its closed state, leaving a portion of the aortic valve opened, which causes a portion of the blood to flow back into the left ventricle. The present invention is structured such that the obstructing device which is attached to one of the cusps is situated in the regurgitant orifice of the aortic valve when the aortic valve is in a closed state and effectively obstructs the valvular insufficiency "opening" at the regurgitant orifice of the aortic valve. Thus, the blood from the aorta does not leak back to the left ventricle (but part of the blood only enters the interior of the hollow tubular member of the obstructing device).

The obstructing device of the present invention comprises a hollow tubular member, attachable to the valve cusp. The hollow tubular member of the obstructing device comprises a proximal opened end, a lateral (side) tubular surface and a closed (sealed) distal end or an end provided with a small hole/orifice (for a wire to pass through as will be explained hereinafter in relation to the delivery of the device). More specifically, the obstructing device hollow tubular member comprises a proximal opening at its proximal end, the substantially tubular surface extending distally from the proximal opening and a closed distal end (or an end provided with a small orifice).

The device is such that when attached to the cusp, either:
1. in case where the distal end is completely closed, blood may enter and thereafter exit the interior of the hollow tubular member from the proximal opening only (i.e. the lateral (side) tubular surface along with the distal side is all closed/sealed).
2. in case where the distal end includes a small orifice, blood may enter and thereafter exit the interior of the hollow tubular member mainly from the proximal opening but a very small portion may exit the distal small orifice. However, this minimally affects the function of the heart and most of the potential leakage blood is obstructed by the obstructing device.

The proximal opening is placed near the proximal end (at the edge) of the cusp, adjacent to its inner side such that when the aortic valve is in a closed state, the obstructing device obstructs the valvular insufficiency "opening" at the regurgitation orifice of the aortic valve.

The obstructing device hollow tubular member is compressible and may be expanded such that the volume of its interior may vary. During systole, when the aortic valve is in its open state, the blood exiting the left ventricle at a substantial current flow causes the obstructing device to partially be compressed and its interior volume to thus decrease. During diastole, when the aortic valve is in its closed state, blood from the aorta may enter the obstructing device interior (possibly adding to its expansion thereof and an increase in the obstructing device interior volume). In any case, during diastole, the blood does not flow back to the left ventricle as it is blocked by the obstructing device which engages the other cusps inner sides and effectively forms a seal not allowing the blood to pass through the engaging locations between the obstructing device and the cusps inner sides (the sides facing the center of the valve). The obstructing device effectively causes the heart native valve to be fully closed when in its closed state, as in the function of a healthy heart. In some embodiments, the present invention obstructing device does not form a total seal (at the regurgitation orifice), but decreases the blood leakage, which also improves the health of a patient.

The opening of the hollow tubular member of the obstructing device (at its proximal side) is attached near the cusp proximal end inner side. The obstructing device extends distally adjacent to and along the cusp that it is attached to. Preferably, the obstructing device tappers distally. In this manner the wide proximal end of the obstructing device hollow tubular member engages the proximal ends of the cusps of the aortic valve (the cusp that it is attached to and the other cusps that their ends tend to close to engage each other) causing the effective seal. The distal part of the obstructing device hollow tubular member attached to the cusp may be narrower than the wide proximal opening, as it is to be attached to the distal portion of the cusp but does not need to be wide in order to obstruct. This configuration enables the obstructing device to have a minimal mass for a most effective function. The proximal opening is configured to be wide enough to obstruct.

According to an embodiment of the present invention, the obstructing device hollow tubular member is in the form of a deformable membrane. The membrane (in the form of the hollow tubular member) comprises a proximal opening, a lateral tubular surface and either:
1. a closed distal end (preferably tapering distally from the opening along the lateral tubular surface to the distal end). The interior of the membrane is completely closed/sealed (except for the proximal opening).
2. a distal end comprising a small orifice, (preferably tapering distally from the opening along the lateral tubular surface to the distal end). The interior of the membrane is closed (except for the proximal opening and the distal end orifice).

During systole the membrane may be partially compressed (by the systole blood flow) and during diastole the membrane may expand as the "leakage" blood enters the interior of the hollow tubular member enlarging its volume.

According to one embodiment the membrane is self-expandable (e.g. elastic). During systole the membrane is partially compressed (by the systole blood flow) and during diastole the membrane expands. The membrane may comprise an artificial source, a biocompatible material (e.g. Dacron, PTFE, etc.) or a biologic source (e.g. animal valve cusp, animal pericard, etc.).

According to another embodiment of the present invention, the obstructing device comprises a frame comprising one or more wires that define its general shape. The wires are structured such that they form a general hollow tubular shape with a closed distal end. The frame wires are structured such that the membrane is attached thereto forming a strengthened hollow tubular member with a proximal opened end, the lateral tubular surface extending distally from the proximal opened end and a closed distal end (optionally with a small orifice). The membrane is actually mounted on the frame. Preferably the frame shape tappers distally.

The present invention obstructing device comprises a grasping arm extending distally from the proximal opening along the external side of the lateral tubular surface of the hollow tubular member with a thin gap between the grasping arm and the external side of the lateral tubular surface. When the obstructing device is inserted, it is mounted on the cusp to which it is attached to, such that the cusp is located within the thin gap. The external side of the lateral tubular surface engages the inner side of the cusp and the grasping arm engages the outer side of the cusp. The grasping arm comprises connecting elements, connectable to the cusp.

FIG. 2A shows an embodiment of the present invention obstructing device 10. The obstructing device 10 comprises a membrane that forms a hollow tapering tubular member 5 with a proximal opening 12. The interior of tapering tubular member 5 is completely closed/sealed by the membrane (except for the proximal opening 12). A lateral tubular surface 6 extends distally from the proximal opening 12, tappers distally and terminates at the closed distal end 7 (wherein in other embodiments (not shown) the distal end may comprise a very small orifice/hole).

FIG. 2B shows an embodiment of the present invention obstructing device 10 comprising a frame comprising one or more wires that define its general shape. The membrane of the obstructing device 10 (not shown) is attached to the frame, such that the frame and membrane attached thereto form together a hollow tapering tubular member 5 with a proximal opening 12 (wherein the interior of tapering tubular member 5 is completely closed/sealed by the membrane except for the proximal opening 12). In one embodiment the frame is external to the membrane layer. In another embodiment, the wires of the frame may be contained within the layer of the membrane.

The tapering tubular member 5 comprises a round (preferably circular) wire portion on its proximal side forming the proximal opening 12. The tapering tubular member 5 comprises one or more longitudinal wire elements 13 along its length. The tapering tubular member 5 comprises one or more transverse wire elements surrounding one or more respective transverse portions of the tapering tubular member 5 placed along its length. The embodiment of FIG. 2B shows three transverse surrounding wire portions 14, 15, 16, each in the form of a sinusoidal wave. Since the tapering tubular member 5 tappers distally, in case of each two adjacent transverse surrounding wire portions, the more proximal one of the two is larger (i.e. it surrounds a longer width portion) than the more distal one of the two. In this case, wire portion 14 is greater that wire portion 15, which is greater than wire portion 16.

The present invention obstructing device 10 comprises a grasping arm 20 (shown in FIGS. 2A and 2B) that fixes device 10 to the cusp. It should be noted that FIG. 2C illustrates the tapering hollow tubular member 5 alone without the grasping arm 20. The grasping arm 20 is fixed to the proximal opening 12 and extends distally therefrom, along the external side surface of the hollow tapering tubular member 5 (along the lateral tubular surface 6) with a thin gap 22 therebetween. When the obstructing device 10 is inserted to the patient's body, it is mounted on the cusp, such that the cusp is located within the thin gap 22 (in between the lateral tubular surface 6 and the inner side of the grasping arm 20). The external surface of lateral tubular surface 6 of tapering tubular member 5 engages the inner side of the cusp (the side facing the center of the valve) and the grasping arm 20 engages the outer side of the cusp (the side facing the blood vessel wall, i.e. the ascending aorta side wall).

The grasping arm 20 comprises connecting elements 25, connectable to the cusp. Preferably, the connecting elements are located at a distal portion of the grasping arm 20. The connecting elements 25 in FIGS. 2A-2B are biocompatible needles that substantially extend proximally (slanting from the grasping arm 20) from the inner side of 10 the grasping arm 20. In this manner, the obstructing device may be inserted without the biocompatible needles 25 injuring the cusp, as the cusp goes through gap 22. When the obstructing device 10 is fully inserted, the biocompatible needles 25 pierce the cusp outer side and thus permanently fix the obstructing device 10 to the cusp.

Preferably, an external surface portion of the lateral tubular surface 6 of the tapering tubular member 5 (typically a portion that faces the grasping arm 20) comprises connecting elements 26, connectable to the cusp. Preferably, the connecting elements are located at a distal portion of the external surface portion of the lateral tubular surface 6 that faces the grasping arm 20. The connecting elements 26 in FIGS. 2A-2B are biocompatible needles that substantially extend proximally (slanting from the lateral tubular surface 6) from the external surface portion of the lateral tubular surface 6 that faces the grasping arm 20. In this manner, the obstructing device 10 may be inserted without the biocompatible needles 26 injuring the cusp, as the cusp goes through gap 22. When the obstructing device 10 is fully inserted, the biocompatible needles 26 pierce the cusp inner side and thus assist in fixing the obstructing device 10 to the cusp. Other types of connecting elements may be used, such as biocompatible pins, biocompatible spikes, etc.

FIG. 3A shows an aortic valve with Aortic Regurgitation in an open state. FIG. 3B shows the aortic valve with Aortic Regurgitation in a closed state, where the leakage opening can be seen. FIG. 3C shows an aortic valve with Aortic Regurgitation in an open state with the obstructing device 10 attached to a valve cusp. In this figure the obstructing device 10 is adjacent to the cusp as the blood flows out of the left ventricle. FIG. 3D shows the aortic valve with Aortic Regurgitation in a closed state, where the leakage opening is obstructed by the obstructing device 10.

FIG. 4A shows a 3D illustration of an Aortic Valve with Regurgitation. The three cusps 130 and the regurgitant orifice 140. FIG. 4B shows FIG. 4A with blood leakage 150. FIG. 4C shows a 3D illustration of the obstructing device 10 inserted in place, within the aortic valve regurgitant orifice 140, configured to obstruct blood leakage.

Figure 5:
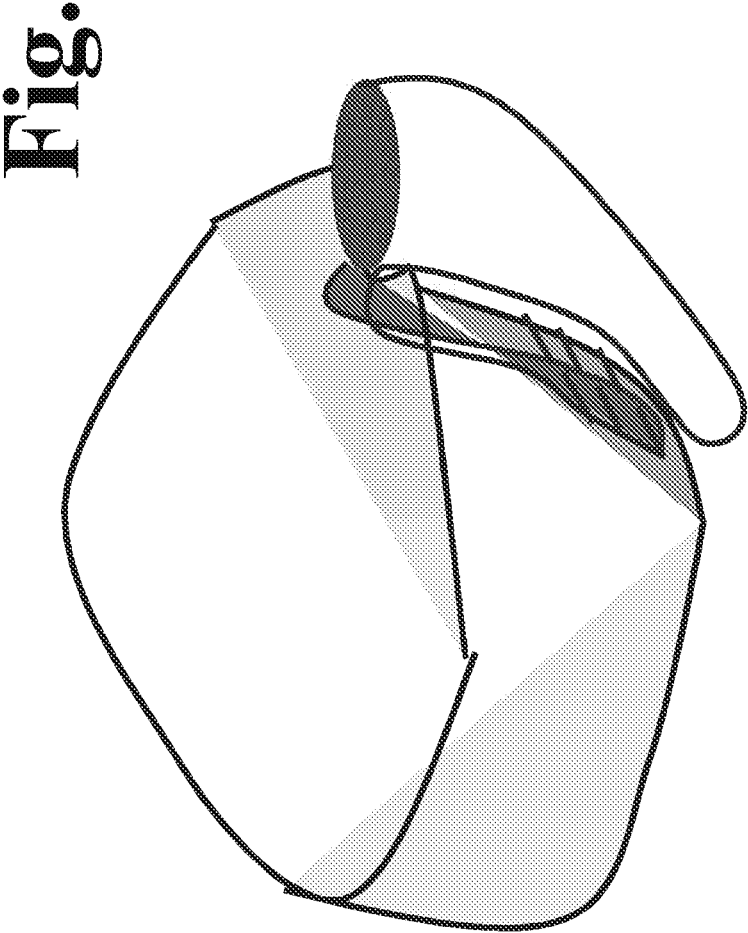
FIG. 5 shows a drawing of the present invention attached to a single cusp.

FIG. 5 shows—the obstructing device 10 attached to a single native or artificial valve.

The frame wires, the grasping arm 20, the connecting elements 25, 26, may be made of a material selected from the group consisting of a shape memory alloy, stainless steel, cobalt chromium and nitinol. The frame is designed to withstand fatigue, to be collapsible and/or self expanding.

The general length of the tapering tubular member 5 and grasping arm 20 is usually between 4 and 8 mm (e.g. 7 mm shown in FIG. 6A).

The diameter of the proximal opening 12 is usually between 6 and 8 mm (shown in FIG. 6A).

The width of the grasping arm 20 is usually between 1 and 4 mm. The thickness of the grasping arm 20 is usually between 0.1 and 2 mm.

The diameter of the frame wires is usually between 0.1 and 1 mm.

The diameter of the connecting elements biocompatible needles 25, 26 is usually between 0.1 and 0.4 mm. The length of the connecting elements biocompatible needles 25, 26 is usually between 4 and 10 mm.

The thickness of the membrane is usually between 0.1 and 1 mm.

Figure 7:
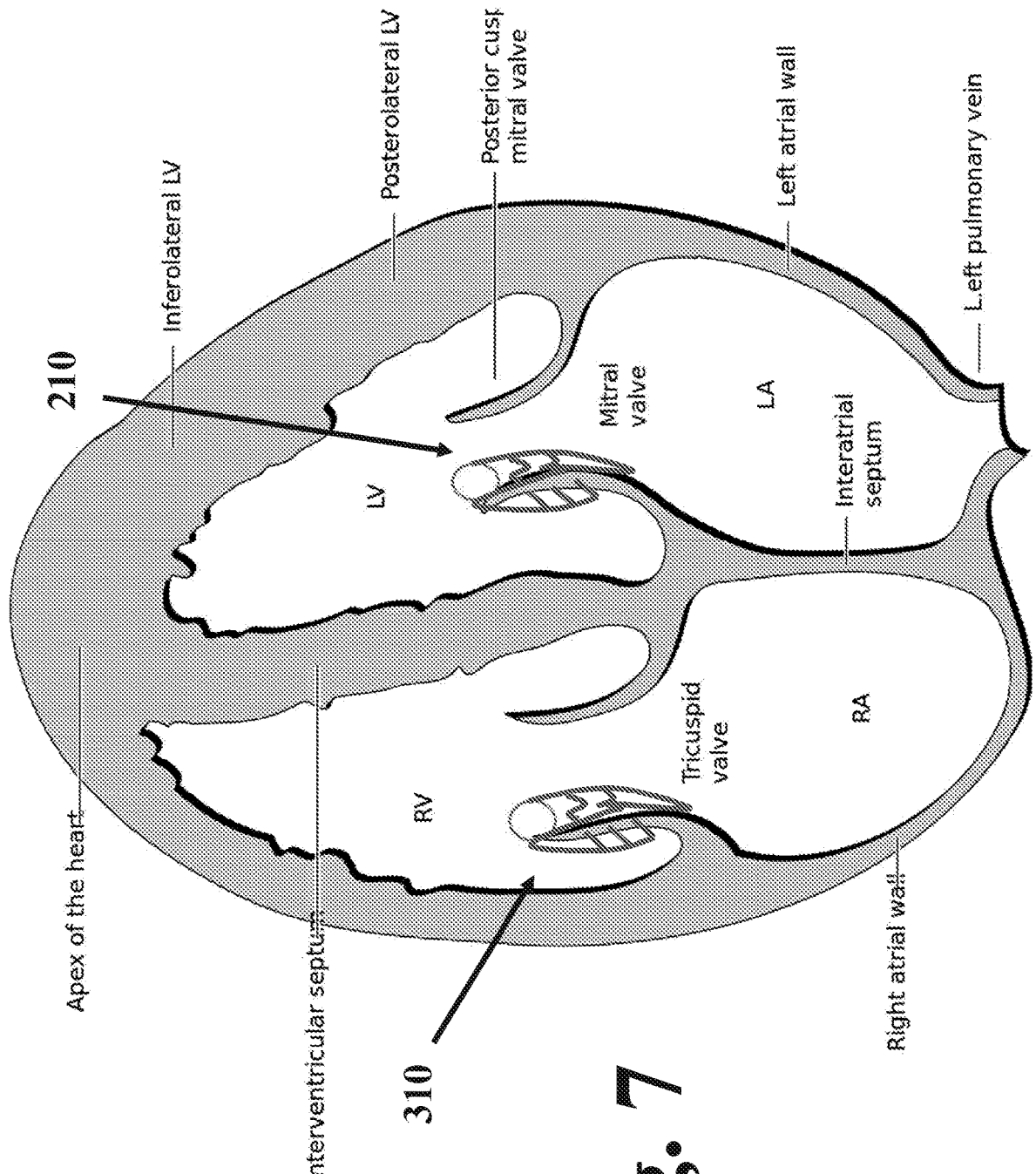
FIG. 7 illustrates examples of embodiments of the present invention on the mitral valve and on the tricuspid valve.

FIG. 7 shows an example of an obstructing device 210 attached to a mitral valve leaflet, and another obstructing device 310 attached to a tricuspid valve leaflet.

The present invention provides a device that closes the malcoaptation gap by filling it with an artificial cusp that self-fits the gap when filled with blood. A potential advantage of the present invention is that is provides a better tolerance to the implantation position than in the prior art leaflet prolongation method (in US 2015/0230919), and a more efficient closure of the gap. Furthermore, a second device can easily be implanted next to the first one if needed.

Figure 8A:
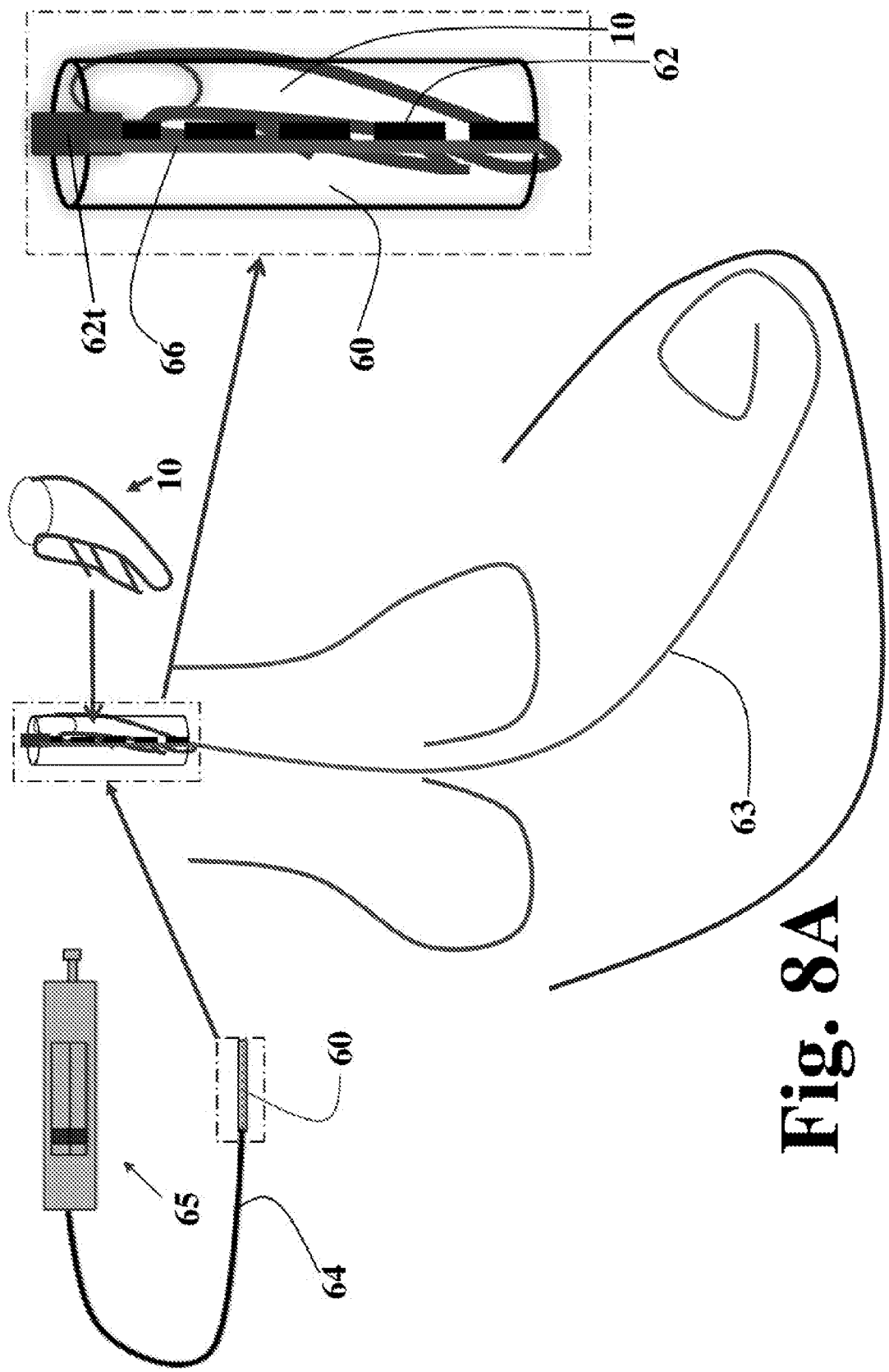
FIGS. 8A-8N illustrate an embodiment of delivery method steps of the present invention method.

The present invention relates to a method for delivering an obstructing device (e.g. the obstructing device as defined herein) via a delivery system to the intended heart valve location, deploying and correctly positioning the obstructing device within the heart valve intended location such that it begins to function by improving the function of the heart valve. FIGS. 8A-8N illustrate the method of delivering the present invention obstructing device 10 to its intended location mounted on a heart valve cusp/leaflet.

The present invention delivery method will be explained in relation to the aorta valve, but may similarly be delivered to the pulmonary valve (and with many aspects to the mitral and tricuspid valves) cusps/leaflets, mutatis mutandis.

According to an embodiment of the present invention, the delivery system comprises an outer sheath 60 and an inner sheath 62 that passes through the outer sheath. The delivery system comprises a guide wire 63 slidably passing through the inner sheath 62. Optionally the guide wire is an extra stiff guide wire. Optionally the guide wire 63 is of type 035. The inner sheath 62 is configured such that guide wire 63 may pass therethrough.

FIG. 6B shows an embodiment of the obstructing device 10 with a proximal loop 71 attached to the proximal opening 12 and a distal loop 72 attached to a distal portion of tapering tubular member 5 (typically at the distal end of tapering tubular member 5). Some embodiments may comprise the proximal loop 71 only, without the distal loop 72.

Preferably, the loops 71 and 72 face each other and are aligned, and extend perpendicularly to the tapering tubular member 5 surface (to the lateral tubular surface 6). The inner sheath 62 passes through the loops 71 and 72. The inner sheath comprises a thickened portion 62t such that it is placed proximally and adjacent to proximal loop 71. In this manner when the sheath 62 is moved distally thickened portion 62t pushes proximal loop 71 distally and thus the whole device 10 distally. Typically, the thickened portion 62t is at a distal portion of inner sheath 62 at a distance from the distal end which is larger than the length of the tapering tubular member 5. The obstructing device 10 during delivery is inside the outer sheath 60 and is in a crimped, compressed or collapsed state (e.g. Crimped to small diameter of less than 7 mm). The device is folded in a passive or compressed state (e.g. pre-load state) in the delivery system.

Grasping arm 20 comprises a loop 75 at its distal end. FIG. 6B shows loop 75 being attached to the distal end of the grasping arm 20 elongated portion. A string 66 extends through an introducer sheath (at the most proximal location where the medical personnel operates the system), through the loop 75 and back to the introducer sheath, such that both ends of string 66 are accessible to the medical personnel operating the system (such that both ends of string 66 extend from the introducer sheath). The grasping arm 20 tends to close always (i.e. tends to be adjacent to the tapering tubular member 5 outer surface, only leaving a small gap 22). When both ends of string 66 are pulled proximally, grasping arm 20 moves away from tapering tubular member 5 outer surface (away from lateral tubular surface 6). When both ends of string 66 are released, grasping arm 20 returns towards tapering tubular member 5 outer surface (towards lateral tubular surface 6). The grasping arm 20 moves in an angular manner from and towards tubular member 5 outer surface (lateral tubular surface 6), as the proximal end of grasping arm 20 is always attached to the proximal opening 12. String 66 may go through the inner sheath in parallel to the guidewire or in a separate dedicated lumen, and exits the inner sheath 62 at an appropriate opening near the grasping arm 20 location in order to pull and open it (to enlarge gap 22).

The diameter of loops 71 and 72 are usually between 0.035" and 0.039".

The diameter of loop 75 is usually between 0.5 and 2 mm.

The delivery system is such that the inner sheath 62 is placed within a delivery tube 64 and extends distally therefrom, wherein they are connected such that they move distally together and proximally together. In the delivery system the outer sheath 60 (in an initial stage the inner sheath 62 is within the outer sheath 64) is attached to the distal end of the delivery tube 64 and can be pulled proximally such that the outer sheath 60 goes over the distal end of the delivery tube 64 in a coaxial manner. In any case, the outer sheath 60 and delivery tube 64 are connected such that they move distally together and proximally together (except when particularly moving the outer sheath alone as explained hereinafter). The delivery system comprises a proximal handle 65 for controlling the delivery system. The handle 65 is configured to control and move the delivery tube 64 proximally or distally (and thus the inner sheath 62 and outer sheath 60) accordingly. Another feature of the handle 65 is that it is configured to control and retract the outer sheath 60 proximally so that it goes over the distal end of the delivery tube 64 in a coaxial manner (for the unsheathing of the device 10). The outer sheath 60 may also be moved distally.

It should be noted that the guide wire 63 may pass through the orifice of the distal end of the hollow tubular member 5, which may contribute to the stability of the procedure.

The method for delivering the obstructing device comprises the following steps.

Making a skin incision (e.g. in the groin).

Creating an opening in a blood vessel (e.g. the femoral artery) and inserting an introducer sheath (e.g. a 6 Fr introducer sheath).

Optionally inserting a closure device.

Inserting a stiff guide wire 63 through the introducer sheath and passing it through the femoral artery.

Optionally Replacing the 6 Fr introducer sheath with a large 11 to 16 Fr introducer sheath.

Optionally replacing the stiff guide wire with a regular guide wire and advancing it all the way up to the aorta and through the opening in the aortic valve and into the left ventricle. Preferably, the guide wire is placed such that it contours to the inner cavity of the left ventricle all the way to the apex, preferably using a pigtail catheter. In some embodiments the first guide wire is the only guide wire inserted for the whole delivery procedure.

Preferably, replacing the regular (soft) guide wire with a stiff guide wire 63.

Passing a delivery catheter system distally (which preferably comprises the delivery tube 64, the outer sheath 60, the inner sheath 62 passing through the outer sheath 60, the present invention obstructing device 10 (with the proximal opening 12 placed at the proximal side and distal end 7 placed at the distal side) wherein the inner sheath 62 passes though the loops 71 and 72, and the thickened portion 62t which is placed proximally and adjacent to proximal loop 71 of device 10). The inner sheath 62 passes in an "over the wire delivery" manner over wire 63 (while wire 63 passes through inner sheath 62).

Figure 8B:
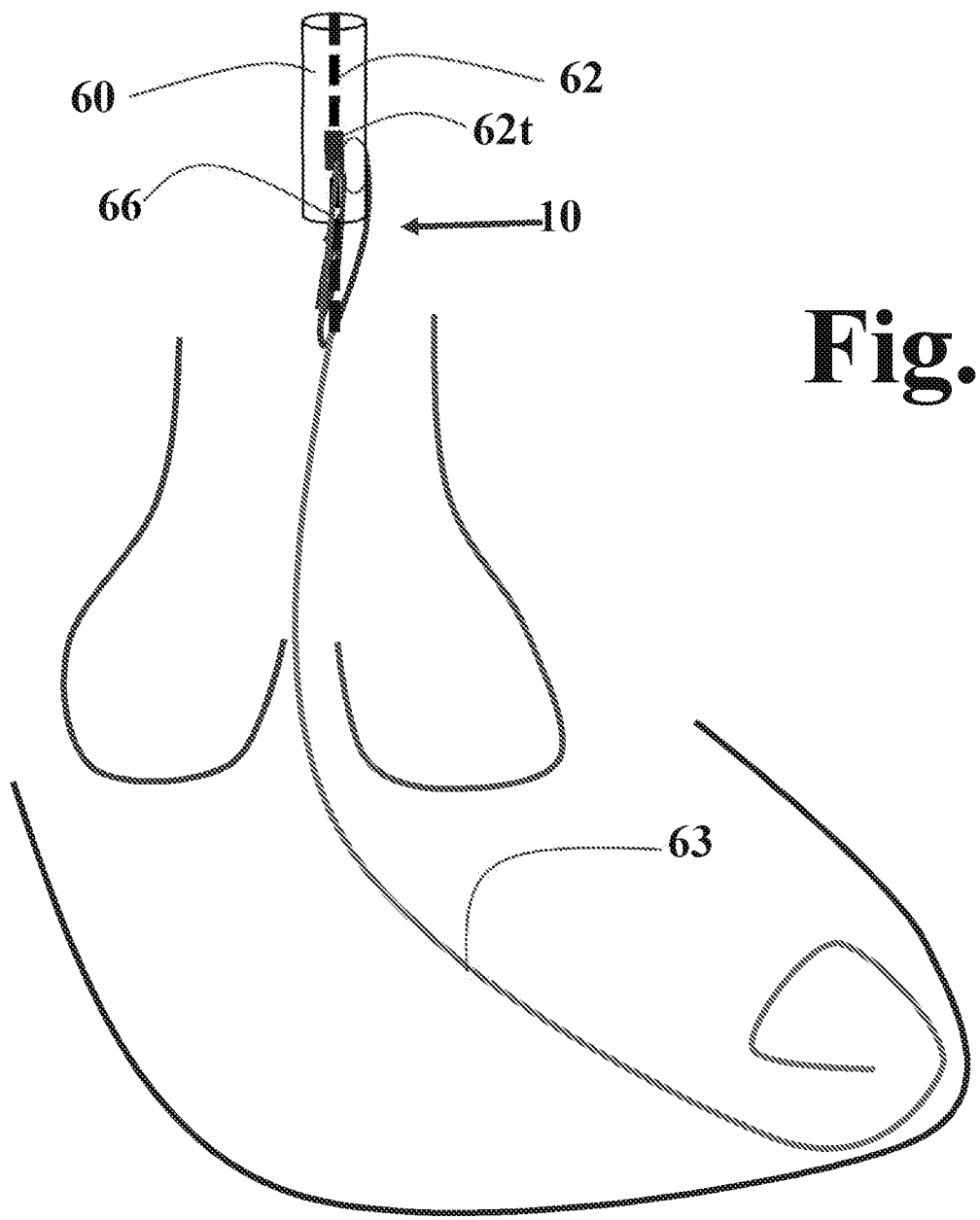
Figure 8C:
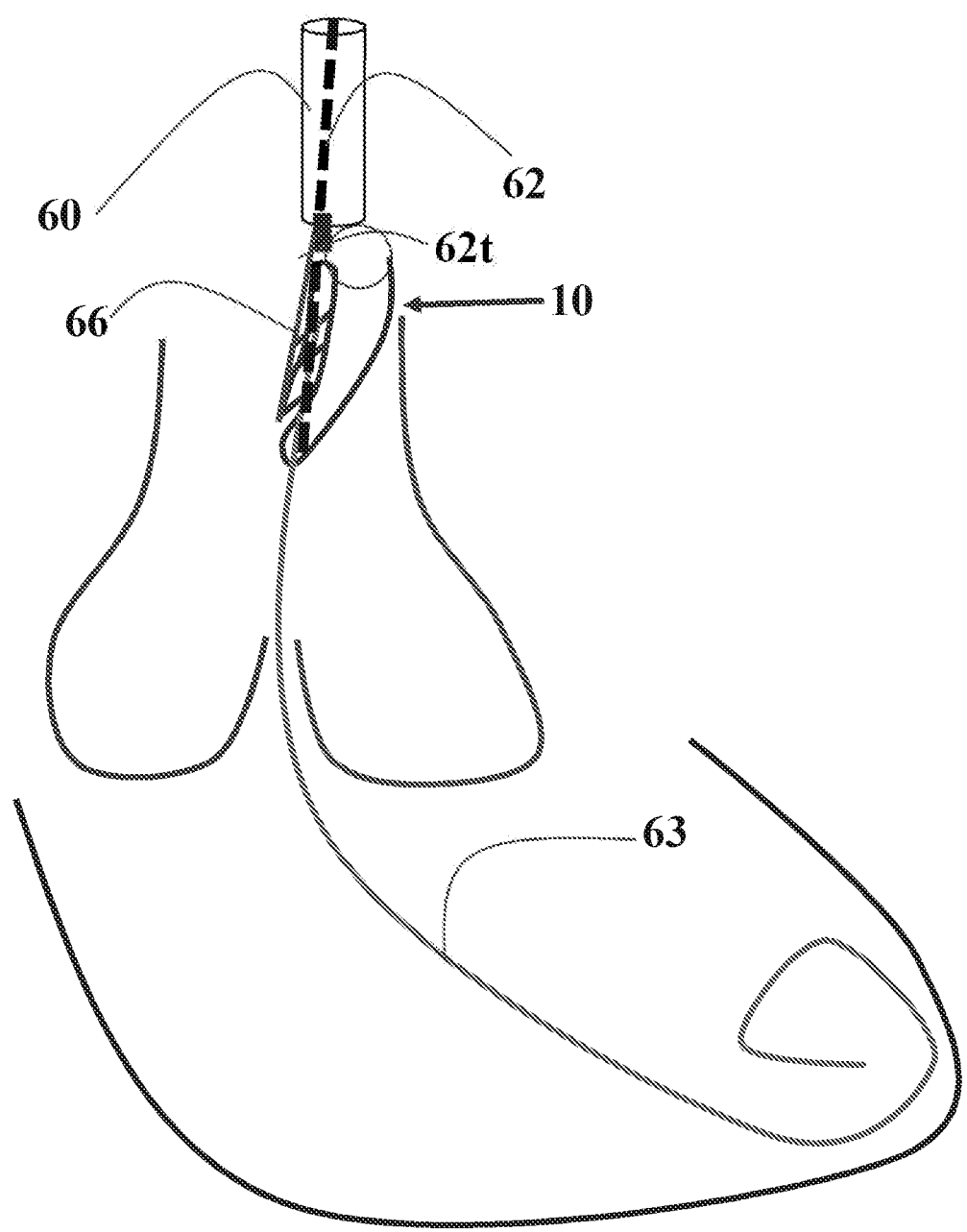

When the distal portion of the inner sheath arrives at the ascending aorta (as in FIG. 8A), retrieving the outer sheath 60 proximally (unsheathing the obstructing device 10) thus beginning to release the obstructing device 10 (FIG. 8B). During this stage the inner sheath 62, with the present invention proximal loop 71 adjacent to thickened portion 62t, are stationary while the outer sheath 60 moves proximally. Once the outer sheath 60 is proximally retrieved backwards the present invention obstructing device 10 becomes fully released from the outer sheath 60 (FIG. 8C). It should be noted that FIG. 8A shows the handle 65, the delivery tube 64 and the outer tube 60. The outer tube 60 and its contents are shown enlarged, and even more enlarged.

Figure 8D:
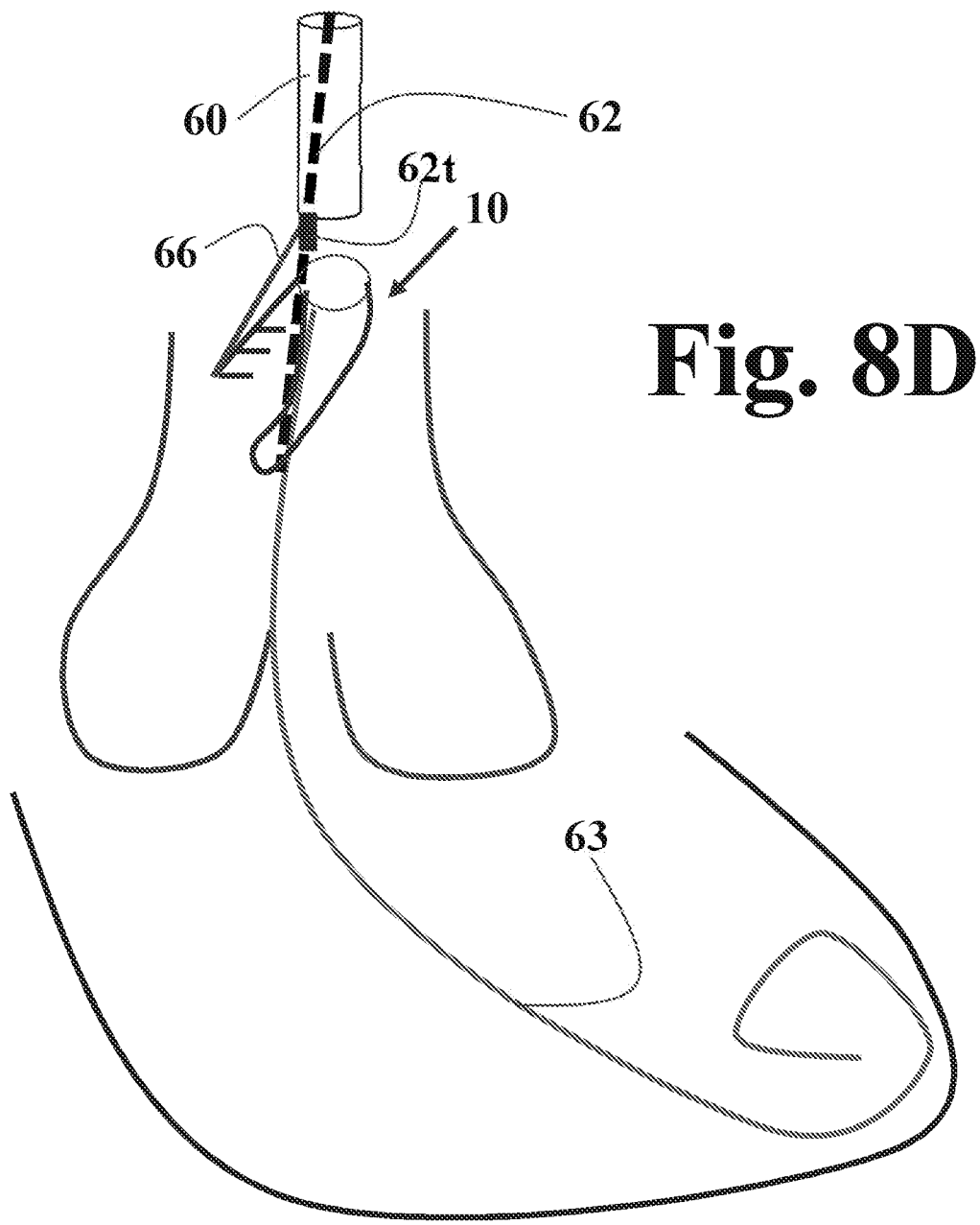

Then the two ends of string 66 are pulled proximally, opening grasping arm 20 (FIG. 8D).

Figure 8E:
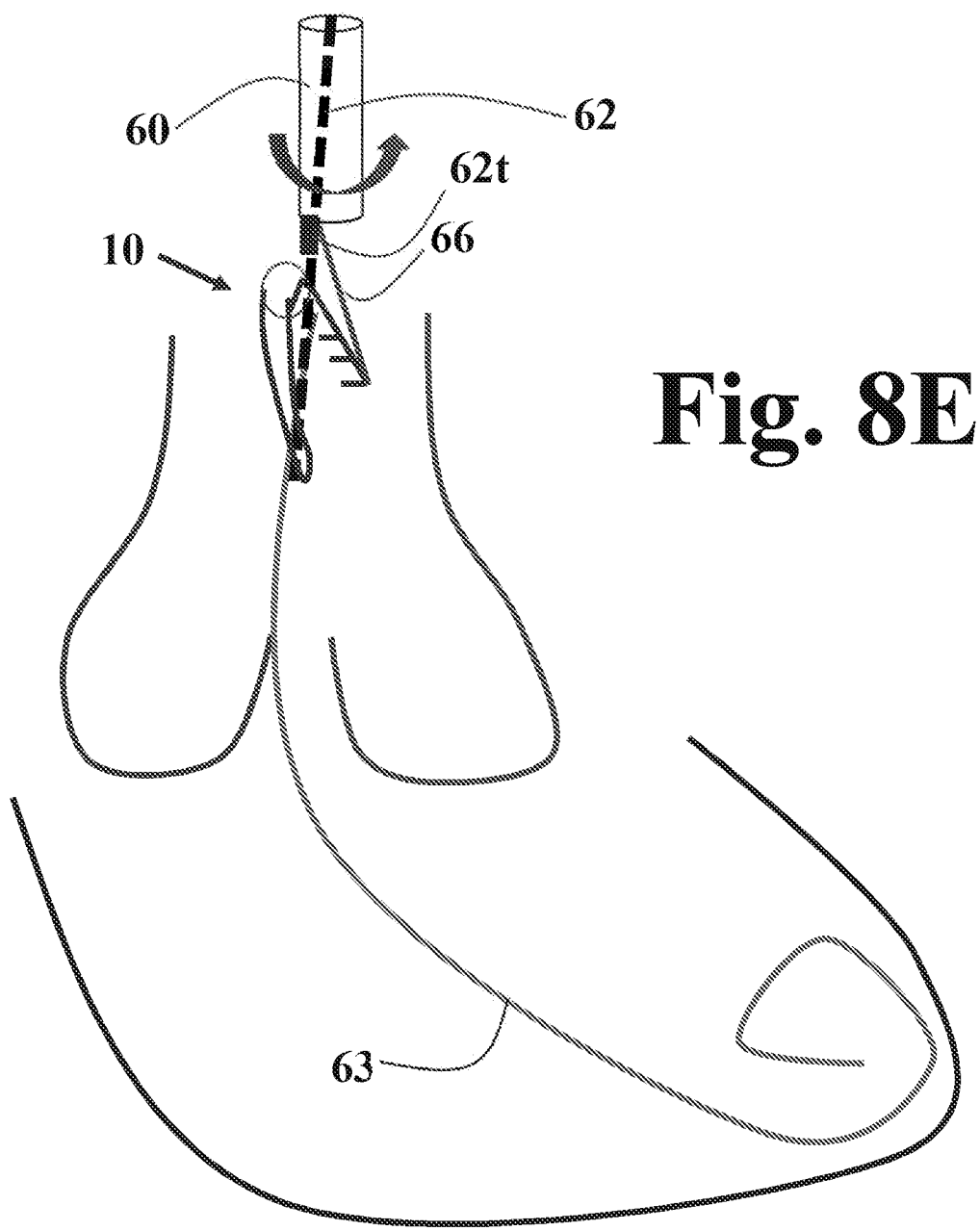

The next step comprises positioning the present invention obstructing device 10 in the correct intended position prior to attaching it to the cusp (FIGS. 8E-8F). This positioning comprises rotating the obstructing device 10 such as to be attached to the cusp, based on imaging modality by manipulating the delivery system such as clock or counter-clock rotation. This is carried out by rotating the delivery tube 64 (by handle 65) which in turn rotates the inner sheath 62, the outer sheath 60 and the device 10.

Figure 8G:
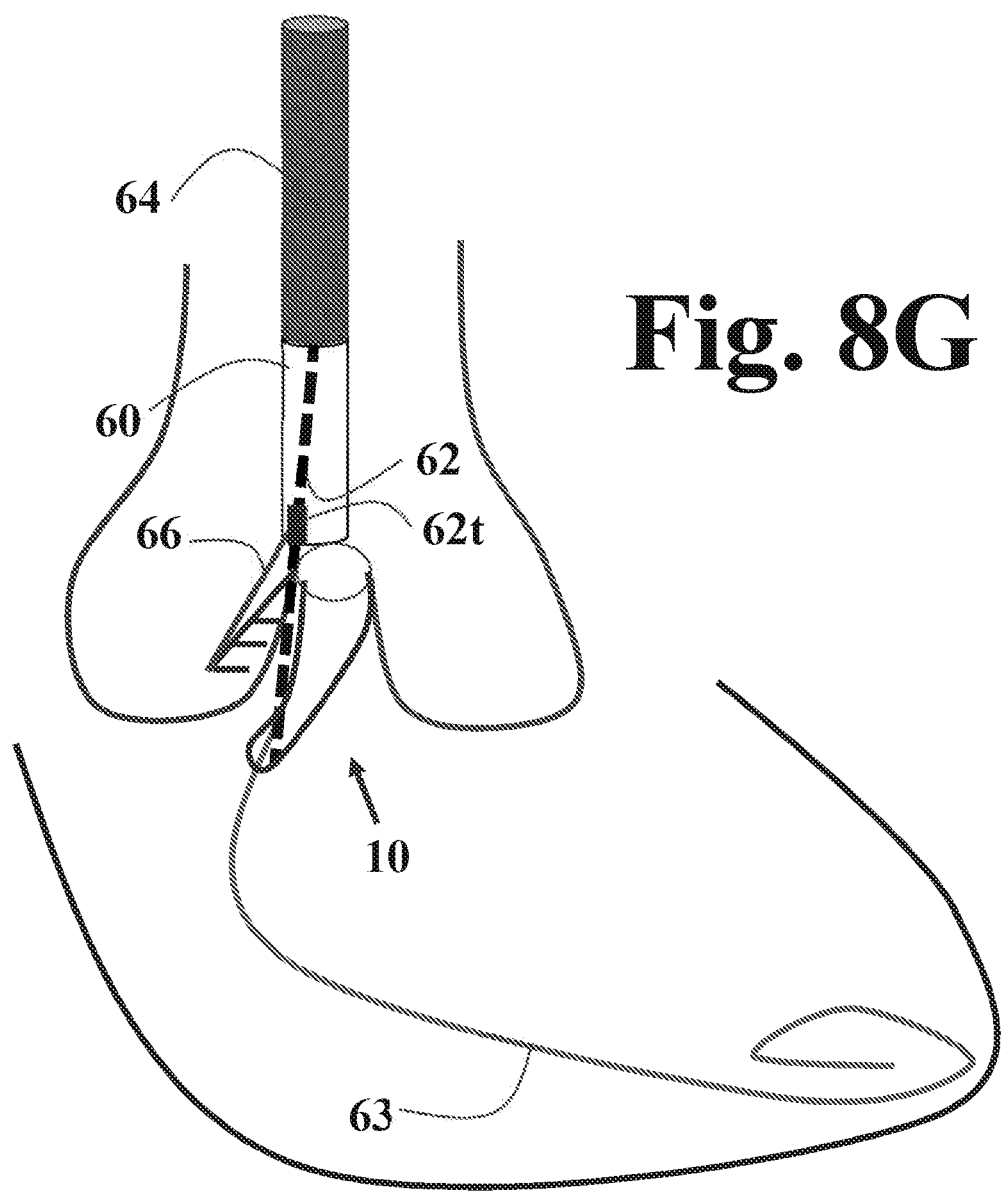

Once at the required position (e.g. to engage the predetermined aortic cusp) the obstructing device 10 is pushed forward (by the inner sheath 62 thickened portion 62t pushing proximal loop 71 distally) against the native aortic cusp being adjacent thereto (FIG. 8G).

Then, the two ends of string 66 are released distally causing grasping arm 20 to close (FIG. 8H), as the grasping arm 20 always tends to close. The connecting elements 25 connect to the cusp e.g. pierce the cusp outer side. Thus, the obstructing device 10 is fully deployed. Optionally, the connecting elements 26 on the lateral tubular surface 6 also pierce the cusp inner side strengthening the connection. Optionally once final positioning is confirmed a diathermia device is applied through the string 66 further fixing the device to the cusp. The string 66 may comprise nitinol and/or may comprise other conductive materials.

The delivery tube 64 including the inner sheath 62 therewithin and the outer sheath 60 thereon, are proximally retrieved in an "over the wire" manner (FIG. 8I).

Figure 8J:
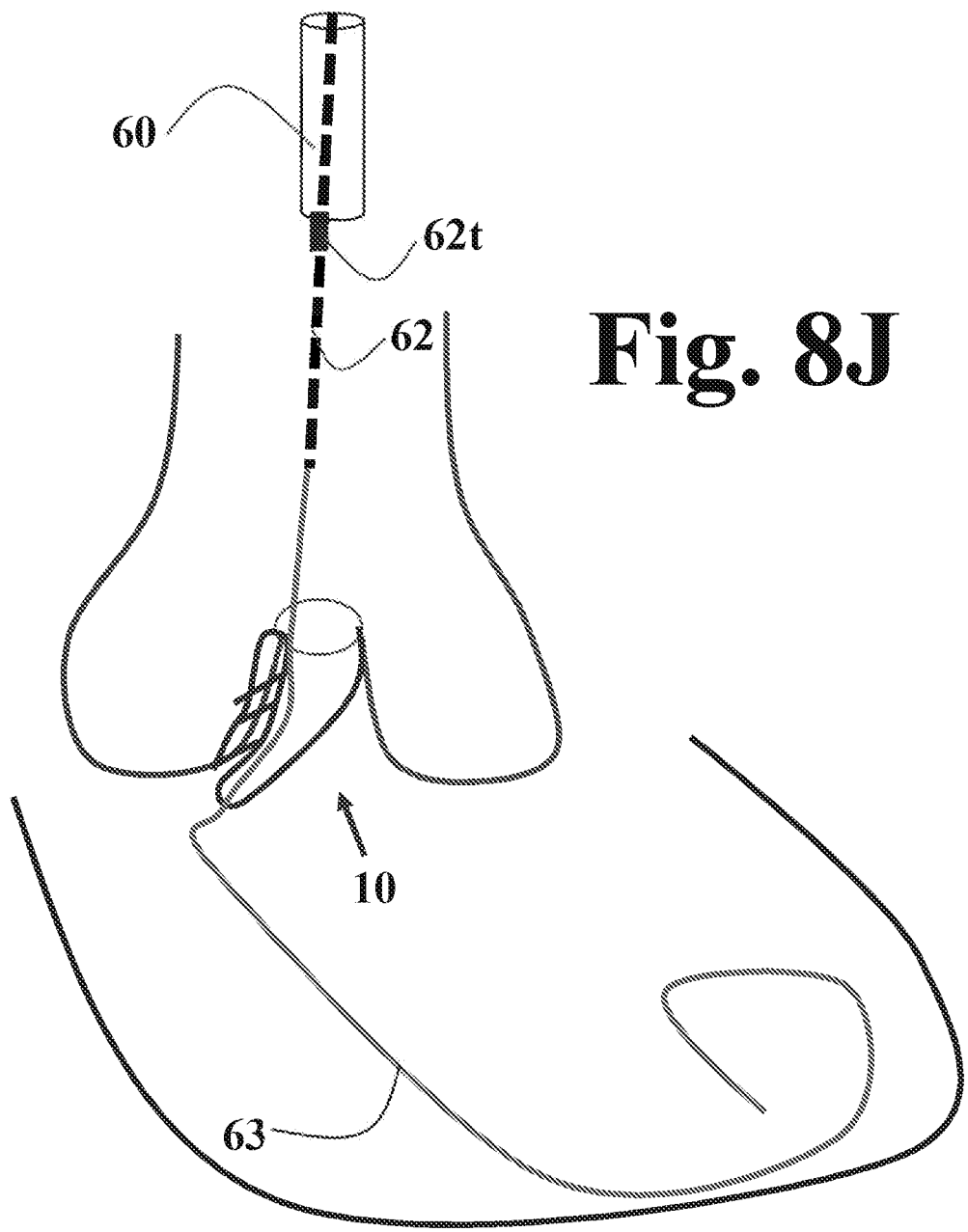

Then, one end of string 66 is pulled proximally while the other end moves distally until it exits the loop 75 and then also returns proximally until being fully retrieved (FIG. 8J).

Figure 8K:
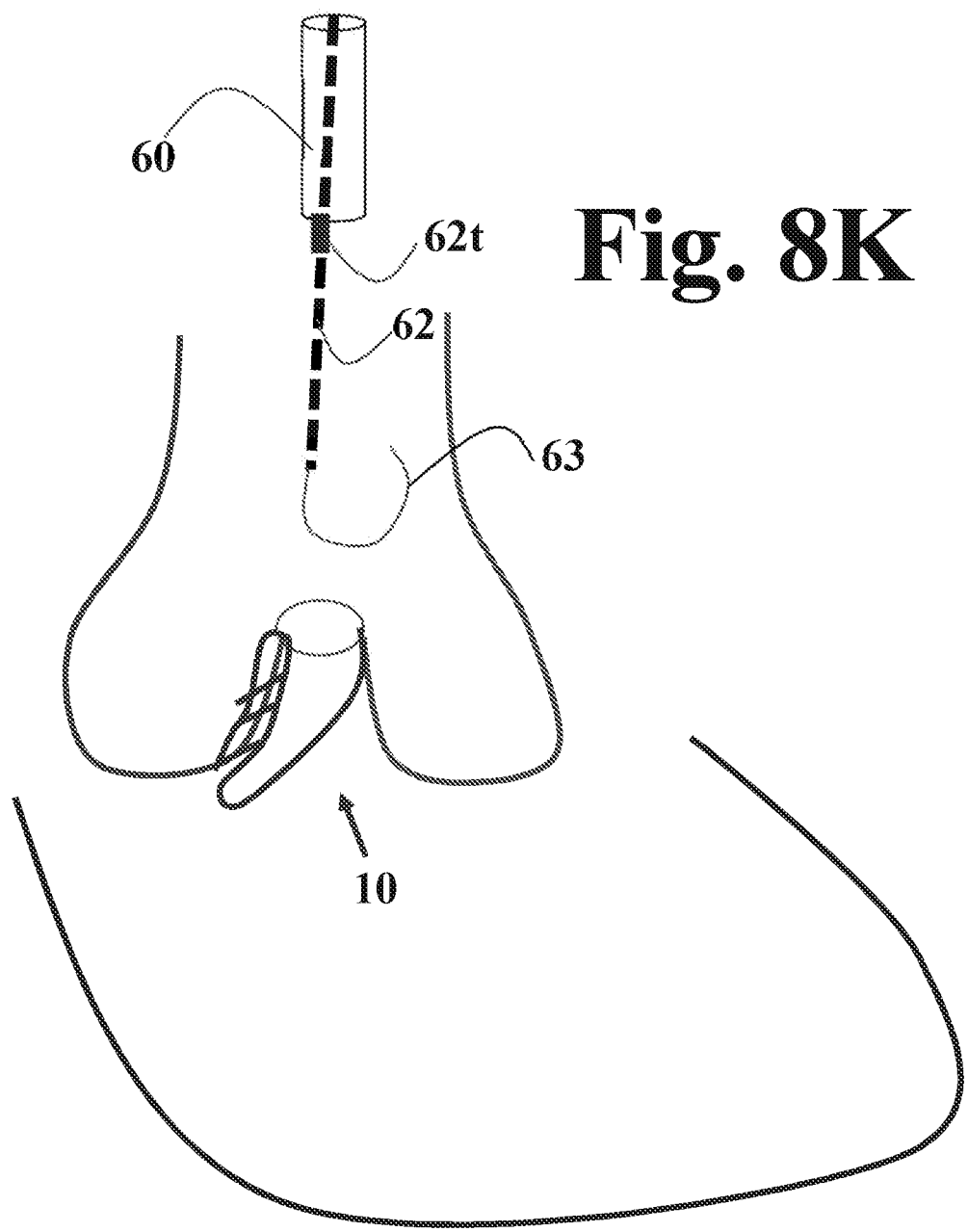
Figure 8L:
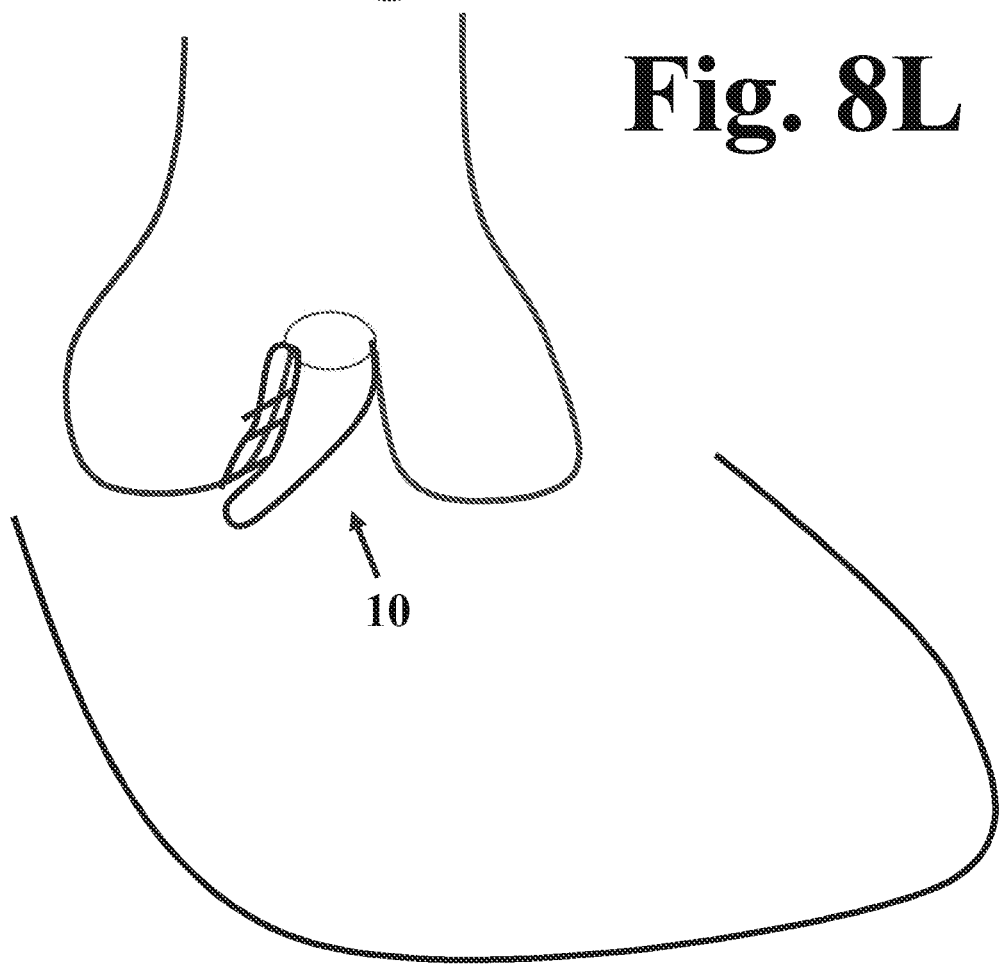

The guide wire 63 is then proximally retrieved (as shown in FIGS. 8K-8L).

Then the introducer sheath is removed and the artery is closed.

FIG. 8M shows the device functioning in a valve opened state and FIG. 8N shows the device functioning in a valve closed state preventing blood leakage into the left ventricle.

It should be noted that some embodiments of the method may be carried out without the outer sheath, mutatis mutandis.

According to another aspect of the present invention, for delivery to the mitral and tricuspid valves, the obstructing device 10 is mounted in the opposite direction within the delivery system i.e. with the opened portion distally and the closed portion proximally. According to this aspect of the present invention the terms "distal" and "proximal" defining the elements of the obstruction device 10 are switched, e.g. the opening (12) will be referred to as the distal opening, the grasping arm (20) extends proximally, the proximal loop (71) will be referred to as the distal loop the distal loop (72) will be referred to as the proximal loop etc., mutatis mutandis. The obstruction device will be referenced 110.

According to this aspect of the present invention the delivery system and method of insertion are almost the same, and the following portion will mainly emphasize on the differences.

Figure 9:
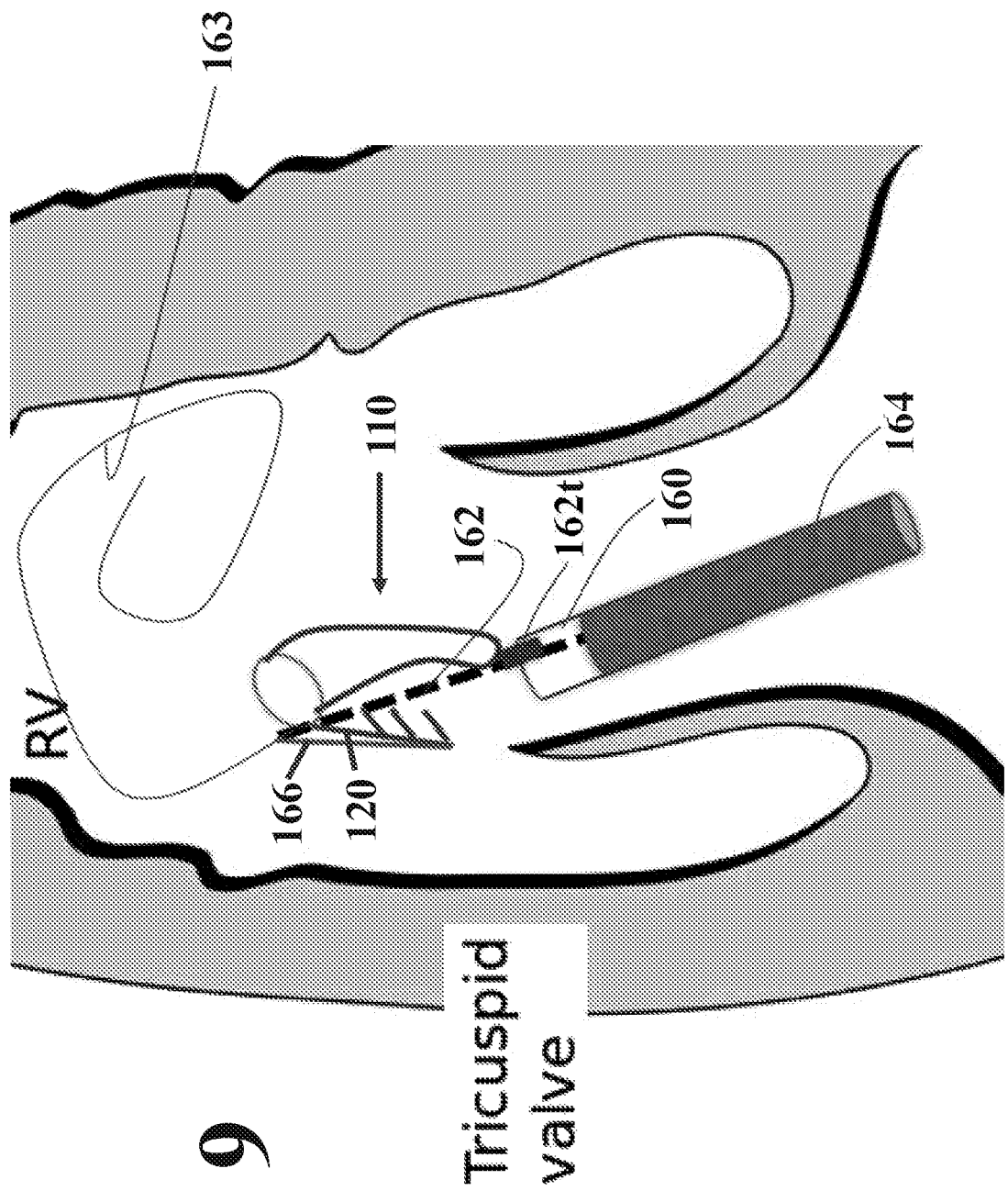
FIG. 9 illustrates one step of the delivery method according to an embodiment of the present invention.

Reference is made to FIG. 9 that shows one step of the insertion method (for delivery to the tricuspid valve). The inner sheath passes through the proximal and distal loops. The inner sheath comprises a thickened portion 162t such that it is placed proximally and adjacent to the proximal loop (not shown). In this manner when the inner sheath 162 is moved distally thickened portion 162t pushes the proximal loop distally and thus the whole device 110 distally.

The grasping arm 120 comprises a loop connected to its proximal end. A string 166 extends from an introducer sheath (at the most proximal location where the medical personnel operates the system), through the grasping arm loop and back to the introducer sheath, such that both ends of string 166 are accessible to the medical personnel operating the system (such that both ends of string 166 extend from the introducer sheath). The grasping arm tends to close always. When both ends of string 166 are pulled proximally, the grasping arm moves away from the tapering tubular member outer surface (away from lateral tubular surface). When both ends of string 166 are released, the grasping arm returns towards the tapering tubular member outer surface (towards the lateral tubular surface). The grasping arm moves in an angular manner from and towards the tubular member outer surface as the distal end of grasping arm is always attached to the distal opening of the obstructing device 110. For this function the string 166 exits the inner sheath 162 via an opening at a location near and distal to the obstructing device 110 distal loop, e.g. at the distal end of the inner sheath 162 as shown in FIG. 9. String 66 may go through the inner sheath 162 in parallel to the guidewire or in a separate dedicated lumen.

The method for delivering the obstructing device comprises the following steps.

Making a skin incision (e.g. in the groin).

Creating an opening in a blood vessel (e.g. the femoral artery) and inserting an introducer sheath (e.g. a 6 Fr introducer sheath).

Optionally inserting a closure device.

Inserting a stiff guide wire 163 through the introducer sheath and passing it through the femoral artery.

Optionally Replacing the 6 Fr introducer sheath with a large 11 to 16 Fr introducer sheath.

Optionally replacing the stiff guide wire with a regular guide wire and advancing it all the way to the right atrium through the Tricuspid valve and to the right ventricle (or left atrium, Mitral valve, left ventricle, mutatis mutandis). Preferably, the guide wire is placed such that it contours to the inner cavity of the respective ventricle all the way to the apex, preferably using a pigtail catheter. In some embodiments the first guide wire is the only guide wire inserted for the whole delivery procedure.

Preferably, replacing the regular (soft) guide wire with a stiff guide wire 163.

Passing a delivery catheter system distally (which preferably comprises the delivery tube 164, the outer sheath 160, the inner sheath 162 passing through the outer sheath 160, the present invention obstructing device 110 (with the distal opening placed at the distal side and proximal end placed at the proximal side) wherein the inner sheath 162 passes though the obstructing device 110 loops, and the thickened portion 162t which is placed proximally and adjacent to the obstructing device 110 proximal loop. The inner sheath 162 passes in an "over the wire delivery" manner over wire 163 (while wire 163 passes through inner sheath 162).

When the distal portion of the inner sheath 162 passes through the tricuspid valve (or mitral valve) and enters the right (or left) ventricle, retrieving the outer sheath 160 proximally (unsheathing the obstructing device 110) thus beginning to release the obstructing device 10. During this stage the inner sheath 162, with the present invention proximal loop adjacent to thickened portion 162t, are stationary while the outer sheath 160 moves proximally. Once the outer sheath 160 is proximally retrieved backwards the present invention obstructing device 110 becomes fully released from the outer sheath 160 (FIG. 8C).

Then the two ends of string 166 are pulled proximally, opening grasping arm 120 (as shown in FIG. 9).

The next step comprises positioning the present invention obstructing device 110 in the correct intended position prior to attaching it to the cusp. This positioning comprises rotating the obstructing device 110 such as to be attached to the cusp, based on imaging modality by manipulating the delivery system such as clock or counter-clock rotation. This is carried out by rotating the delivery tube 164 (by the delivery system handle) which in turn rotates the inner sheath 162, the outer sheath 160 and the device 110.

Once at the required position (e.g. to engage the predetermined cusp/leaflet) the obstructing device 110 is pulled proximally (the string 166 coming out of the opening of the inner sheath 162 distal to the distal loop and thus effectively hooking the distal loop, pushes the distal loop proximally, and thus the entire device 110 proximally), until the cusp/leaflet is within the gap between the grasping arm 120 and the hollow tapering tubular member.

Then, the two ends of string 166 are released distally causing grasping arm 120 to close, as the grasping arm 120 always tends to close. The connecting elements 25 connect to the cusp e.g. pierce the cusp outer side. Thus, the obstructing device 110 is fully deployed. Optionally, the connecting elements on the lateral tubular surface also pierce the cusp inner side strengthening the connection. Optionally once final positioning is confirmed a diathermia device is applied through the string 166 further fixing the device to the cusp. The string 166 may comprise nitinol and/or may comprise other conductive materials.

Then, one end of string 166 is pulled proximally while the other end moves distally until it exits the grasping arm loop and then also returns proximally until being fully retrieved. According to this aspect of the invention, the string 166 is retrieved prior to the inner sheath 162 so that the inner sheath 162 may exit the distal loop.

The delivery tube 164 including the inner sheath 162 therewithin and the outer sheath 160 thereon, are proximally retrieved in an "over the wire" manner.

The guide wire 163 is then proximally retrieved.

Then the introducer sheath is removed, and the artery is closed.

It should be noted that even according to this aspect of the present invention, some embodiments of the method may be carried out without the outer sheath, mutatis mutandis.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. An obstructing device configured for deployment in an aortic valve, and for attachment to a leaflet of the aortic valve, comprising:
   a hollow tubular member comprising:
   a. a proximal opening at its proximal end, configured to be faced toward the aorta;
   b. a substantially tubular surface extending distally from said proximal opening, configured to extend toward the left ventricle;
   c. a distal end;

a grasping arm extending distally from said opening at the proximal end and configured for anchoring said obstructing device to an aortic valve leaflet;

wherein said hollow tubular member is tapered asymmetrically so that the obstructing device is configured to extends distally toward the left ventricle, and is configured to extend adjacent to and along the leaflet;

wherein the distal end is either closed or comprises a small orifice; and wherein said hollow tubular member is soft enough to radially collapse when blood flows outside and along said tubular surface from the distal end towards the proximal end and wherein said tubular member fills with blood and expands to reduces regurgitation through the aortic valve when the aortic valve closes on said hollow tubular member.

2. The obstructing device according to claim 1, wherein the boll tubular member comprises a membrane.

3. The obstructing device according to claim 2, wherein the membrane is self-expandable.

4. The obstructing device according to claim 2, further comprising a frame comprising one or more wires; wherein the membrane is mounted on said frame.

5. The obstructing device according to claim 1, wherein the hollow tubular member tapers distally.

6. The obstructing device according to claim 1, wherein a thin gap is formed between the grasping arm and the substantially tubular surface.

7. The obstructing device according to claim 1, wherein the grasping arm comprises a first group of connecting elements configured to anchor said device to an aortic valve leaflet.

8. The obstructing device according to claim 7, wherein the first group of connecting elements are selected from the group consisting of biocompatible needles, biocompatible pins and biocompatible spikes.

9. The obstructing device according to claim 8, wherein the first group of connecting elements are biocompatible needles that extend proximally and slant from the grasping arm to pierce an inner side of a cusp of said valve.

10. The obstructing device according to claim 1, wherein the substantially tubular surface comprises a plurality of connecting elements configured to anchor said device to an aortic valve leaflet.

11. The obstructing device according to claim 10, wherein the plurality of connecting elements are selected from the group consisting of biocompatible needles, biocompatible pins and biocompatible spikes to engage a cusp.

12. The obstructing device according to claim 11, wherein the plurality of connecting elements are biocompatible needles that extend proximally and slant from the substantially tubular surface.

13. The obstructing device according to claim 1, further comprising a proximal loop attached to the proximal opening.

14. The obstructing device according to claim 13 further comprising a distal loop attached to a distal portion of the hollow tubular member.

15. The obstructing device according to claim 14, wherein the proximal loop and distal loop face each other and are aligned.

16. The obstructing device according to claim 1, wherein the grasping arm comprises a loop at its distal end.

17. A method for implanting an obstructing device according to claim 16 on a heart valve cusp or leaflet, wherein said obstructing device comprises a proximal loop attached to the proximal opening;

wherein said method comprises:

creating an opening in a blood vessel;

inserting an introducer sheath;

inserting a guide wire through the introducer sheath and passing it through the blood vessel all the way to the heart valve and therethrough to the respective heart chamber;

providing an inner sheath passing through the obstructing device proximal loop, and providing that said inner sheath comprises a thickened portion placed proximal to said proximal loop, passing the inner sheath over said guide wire until said device is placed proximal to the respective heart valve;

providing a string inserted through the introducer sheath and passing via an opening in the inner sheath, and passing through the grasping arm loop and back via said opening in the inner sheath to the introducer sheath, such that both ends of said string extend from the introducer sheath, pulling the two ends of said string proximally thereby opening the grasping arm;

positioning the obstructing device to the correct intended position;

pushing the obstructing device distally;

releasing said two ends of said string distally thereby causing the grasping arm to close;

proximally retrieving the inner sheath;

proximally retrieving one end of said string until said string exits the grasping arm loop and continuing to proximally retrieve said string until said string is fully retrieved;

proximally retrieving said guide wire;

removing said introducer sheath.

18. A method for implanting an obstructing device on a heart valve cusp or leaflet, wherein said obstructing device comprises a hollow tubular member comprising:
 a. a distal opening at its distal end;
 b. a substantially tubular surface extending proximally from said distal opening;
 c. a proximal end;

wherein said obstructing device further comprises a grasping arm extending proximally from said opening at the distal end;

wherein the proximal end is either closed or includes a small orifice;

wherein the grasping arm comprises a loop at its proximal end; and wherein said obstructing device comprises a proximal loop attached to a proximal portion of the hollow tubular member;

wherein said method comprises:

creating an opening in a blood vessel;

inserting an introducer sheath;

inserting a guide wire through the introducer sheath and passing it through the blood vessel all the way to the heart valve and therethrough to the respective heart chamber;

providing an inner sheath passing through the obstructing device proximal loop, and providing that said inner sheath comprises a thickened portion placed proximal to said proximal loop, passing the inner sheath over said guide wire until said device is placed in said respective heart chamber;

providing a string inserted through the introducer sheath and passing via an opening in the inner sheath distal to said distal loop, and passing through the grasping arm loop and back via said opening in the inner sheath to the introducer sheath, such that both ends of said string extend from the introducer sheath, pulling the two ends of said string proximally thereby opening the grasping arm;

positioning the obstructing device to the correct intended position;

pulling the obstructing device proximally;

releasing said two ends of said string distally thereby causing the grasping arm to close;

proximally retrieving one end of said string until said string exits the grasping arm loop and continuing to proximally retrieve said string until said string is fully retrieved;

proximally retrieving the inner sheath;

proximally retrieving said guide wire;

removing said introducer sheath.

19. The device according to claim 2, wherein said membrane is formed of pericard.

20. The device according to claim 1, wherein said distal end comprises a small orifice, sized to allow blood flow therethrough when the tubular member is not radially collapsed, but not affecting the function of the heart.

21. The device according to claim 1, configured to be attached to a single cusp.

22. The obstructing device according to claim 7, wherein the substantially tubular surface comprises a second group of connecting elements configured to anchor said device to an aortic valve leaflet.

23. The obstructing device according to claim 1, wherein hollow tubular member does not have a wire framework.

24. A method for implanting an obstructing device on a heart valve cusp or leaflet of the aortic valve, wherein said obstructing device comprises a hollow tubular member comprising:
  a. an opening at one end;
  b. a substantially tubular surface extending from said opening;
  c. a second end;

wherein said obstructing device further comprises a grasping arm extending from said opening at the first end;

wherein said substantially tubular surface tapers asymmetrically;

wherein the second end includes a small orifice allowing hood flow h the device;

wherein said method comprises:

introducing an obstructing device via a blood vessel to an aortic valve;

mounting the obstructing device on an aortic valve leaflet via said grasping arm, such that the opening is facing the aorta and the substantially tubular surface extends toward the left ventricle; the substantially tubular surface extending adjacent to and along the leaflet;

allowing the obstructing device to compress during systole; and allowing the obstructing device to expand during diastole.

25. The obstructing device according to claim 1, wherein said obstructing device is configured to extend distally toward the left ventricle, and is configured to extend adjacent to and along the length of the leaflet.

26. The obstructing device according to claim 1, wherein said obstructing device is configured to extend distally toward the left ventricle, and is configured to extend adjacent to and along the leaflet, and is configured to conform to the curvature of the leaflet.

27. The obstructing device according to claim 1, wherein said obstructing device is configured to extend distally toward the left ventricle, and is configured to curve along the leaflet.

28. The obstructing device according to claim 1, wherein the tubular member bends away from the longitudinal axis, and the grasping is bent to the same direction.

29. The obstructing device according to claim 7, wherein a distal end of the grasping arm comprises connecting elements for connecting to the aortic valve leaflet.

30. The obstructing device according to claim 7, wherein a central section of the grasping arm comprises connecting elements for connecting to the aortic valve leaflet.

31. The obstructing device according to claim 1, wherein said obstructing device comprises a first group of connecting elements and a second group of connecting elements, the two groups arranged to face each other, and configured to connect to the same leaflet.

* * * * *